US012599579B2

(12) United States Patent
Millet et al.

(10) Patent No.: US 12,599,579 B2
(45) Date of Patent: *Apr. 14, 2026

(54) COMPOSITIONS AND COMPOUNDS CONTAINING KETONE BODIES AND/OR KETONE BODY PRECURSORS AND ONE OR MORE AMINO ACIDS

(71) Applicant: AXCESS GLOBAL SCIENCES, LLC, Washington, UT (US)

(72) Inventors: Gary Millet, Salt Lake City, UT (US); Ryan Lowery, Tampa, FL (US); Jacob Wilson, Tampa, FL (US); Terry Lacore, Melissa, TX (US)

(73) Assignee: AXCESS GLOBAL SCIENCES, LLC, Washington, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/261,853

(22) Filed: Jul. 7, 2025

(65) Prior Publication Data

US 2025/0332128 A1      Oct. 30, 2025

Related U.S. Application Data

(63) Continuation-in-part of application No. 18/977,541, filed on Dec. 11, 2024, now Pat. No. 12,350,243, which is a continuation of application No. 18/219,556, filed on Jul. 7, 2023, now Pat. No. 12,251,362, which is a continuation of application No. 17/367,206, filed on Jul. 2, 2021, now Pat. No. 12,109,182, which is a continuation-in-part of application No. 15/491,924, filed on Apr. 19, 2017, now Pat. No. 11,173,138.

(60) Provisional application No. 62/324,798, filed on Apr. 19, 2016.

(51) Int. Cl.
| | |
|---|---|
| *A61K 31/19* | (2006.01) |
| *A61K 9/00* | (2006.01) |
| *A61K 31/522* | (2006.01) |
| *A61P 3/04* | (2006.01) |
| *A61P 25/28* | (2006.01) |

(52) U.S. Cl.
CPC ............ *A61K 31/19* (2013.01); *A61K 9/0053* (2013.01); *A61K 31/522* (2013.01); *A61P 3/04* (2018.01); *A61P 25/28* (2018.01)

(58) Field of Classification Search
CPC ...................................................... A61K 31/19
See application file for complete search history.

(56) References Cited

U.S. PATENT DOCUMENTS

| | | | |
|---|---|---|---|
| 2,238,149 | A | 4/1941 | Aeckerle |
| 2,976,073 | A | 3/1961 | Russell et al. |
| 4,139,761 | A | 2/1979 | Obrowski |
| 4,224,503 | A | 9/1980 | Gijzel et al. |
| 4,292,499 | A | 9/1981 | Kleinschmidt et al. |
| 4,627,808 | A | 12/1986 | Hughes |
| 4,663,166 | A | 5/1987 | Veech |
| 4,771,074 | A | 9/1988 | Lammerant et al. |
| 4,969,393 | A | 11/1990 | Mahlich et al. |
| 4,997,976 | A | 3/1991 | Brunengraber et al. |
| 5,093,044 | A | 3/1992 | Wretlind et al. |
| 5,100,677 | A | 3/1992 | Veech |
| 5,116,868 | A | 5/1992 | Chen et al. |
| 5,288,512 | A | 2/1994 | Seiden |
| 5,292,774 | A | 3/1994 | Hiraide et al. |
| 5,654,266 | A | 8/1997 | Chen et al. |
| 5,700,670 | A | 12/1997 | Yamagishi et al. |
| 6,031,000 | A | 2/2000 | Nissen et al. |

(Continued)

FOREIGN PATENT DOCUMENTS

| | | |
|---|---|---|
| CA | 2990927 A1 | 7/2018 |
| CN | 86108978 A | 11/1987 |

(Continued)

OTHER PUBLICATIONS

Kim Do Young et al., "Ketone bodies are protective against oxidative stress in neocortical neurons," Journal of Neurochemistry, vol. 101, Issue 5, Jun. 1, 2007, pp. 1316-1326.
Kirsch, Jr et al. "Butanediol Induced Ketosis Increases Tolerance to Hypoxia in the Mouse." Stroke. 1980. vol. 11, No. 5, pp. 506-513.
Kossoff, Eric H. et al. "Optimal Clinical Management of Children Receiving the Ketogenic Diet: Recommendations of the International Ketogenic Diet Study Group." Epilepsia, Feb. 2009; 50(2):304-17. Epub Sep. 23, 2008.

(Continued)

*Primary Examiner* — Rei Tsang Shiao
(74) *Attorney, Agent, or Firm* — Workman Nydegger

(57) ABSTRACT

Compositions and methods for administering ketone bodies to a subject include a ketone body or ketone body precursor complexed with or coupled to at least one amino acid. The compositions and methods cause one or more of: weight loss, weight maintenance, reduced blood glucose level, maintenance of blood glucose level, increased muscle and physical performance, enhanced metabolic and cellular repair, improved detoxification and gut health, targeted bioavailability, sustained release and controlled absorption, increased metabolic efficiency, enhanced cellular uptake, minimized side effects, multifunctional therapeutics, improved focus, improved energy, improved cognitive function, improved mental acuity, treatment of traumatic brain injury, treatment of diabetes, treatment of neurological disorder, treatment of cancer, treatment of inflammatory condition, appetite suppression, anti-aging effects, anti-glycation effects, treatment of epilepsy, treatment of depression, improved performance, improved muscle mass, improved motor function, increased strength, increased metabolism, increased fat loss, increased fat oxidation, improved body composition, and improved mood.

22 Claims, 12 Drawing Sheets

(56) References Cited

U.S. PATENT DOCUMENTS

| | | | |
|---|---|---|---|
| 6,207,856 B1 | 3/2001 | Veech | |
| 6,217,915 B1 | 4/2001 | Luchansky et al. | |
| 6,232,345 B1 | 5/2001 | Hiraide et al. | |
| 6,316,038 B1 | 11/2001 | Veech | |
| 6,323,237 B1 | 11/2001 | Veech | |
| 6,380,244 B2 | 4/2002 | Martin et al. | |
| 6,613,356 B1 | 9/2003 | Vlahakos | |
| 6,706,756 B1 | 3/2004 | Fitzpatrick et al. | |
| 6,835,750 B1 | 12/2004 | Henderson | |
| 7,351,736 B2 | 4/2008 | Veech | |
| 7,807,718 B2 | 10/2010 | Hashim et al. | |
| 7,891,287 B2 | 2/2011 | Miller | |
| 8,071,641 B2 | 12/2011 | Weiss et al. | |
| 8,101,653 B2 | 1/2012 | Veech | |
| 8,124,589 B2 | 2/2012 | Henderson | |
| 8,344,896 B2 | 1/2013 | Ozanne | |
| 8,426,468 B2 | 4/2013 | Henderson | |
| 8,642,654 B2 | 2/2014 | Clarke et al. | |
| 8,748,400 B2 | 6/2014 | Henderson | |
| 9,138,420 B2 | 9/2015 | D'Agostino et al. | |
| 9,186,340 B2 | 11/2015 | Andrews et al. | |
| 9,211,275 B2 | 12/2015 | Clarke et al. | |
| 9,435,566 B2 | 9/2016 | Hill et al. | |
| 9,675,577 B2 | 6/2017 | D'Agostino et al. | |
| 9,717,767 B2 | 8/2017 | Carpenter et al. | |
| 9,795,580 B2 | 10/2017 | Weeber et al. | |
| 9,808,481 B2 | 11/2017 | Ritter et al. | |
| 9,925,164 B1 | 3/2018 | Hashim | |
| 9,957,246 B2 | 5/2018 | Stinchcomb et al. | |
| 10,022,409 B2 | 7/2018 | Carpenter et al. | |
| 10,051,880 B2 | 8/2018 | Clarke et al. | |
| 10,088,197 B2 | 10/2018 | Hamagami et al. | |
| 10,154,982 B2 | 12/2018 | Clarke et al. | |
| 10,245,242 B1 | 4/2019 | Millet | |
| 10,245,243 B1 | 4/2019 | Millet | |
| 10,278,961 B2 | 5/2019 | Lowery et al. | |
| 10,292,592 B2 | 5/2019 | Marshall et al. | |
| 10,292,952 B2 | 5/2019 | Millet | |
| 10,407,331 B2 | 9/2019 | Kamito et al. | |
| 10,512,615 B1 | 12/2019 | Millet | |
| 10,588,876 B2 | 3/2020 | Millet | |
| 10,588,877 B2 | 3/2020 | Arnold | |
| 10,596,128 B2 | 3/2020 | Millet | |
| 10,596,129 B2 | 3/2020 | Millet | |
| 10,596,130 B2 | 3/2020 | Millet | |
| 10,596,131 B2 | 3/2020 | Millet | |
| 10,660,958 B2 | 5/2020 | Clarke | |
| 10,736,861 B2 | 8/2020 | Millet | |
| 10,792,269 B2 | 10/2020 | Hashim | |
| 10,925,843 B2 | 2/2021 | Millet | |
| 10,973,786 B2 | 4/2021 | Millet | |
| 10,980,764 B1 | 4/2021 | D'Agostino et al. | |
| 10,980,772 B2 | 4/2021 | Millet | |
| 11,020,362 B2 | 6/2021 | Millet | |
| 11,026,929 B2 | 6/2021 | Lowery et al. | |
| 11,033,553 B2 | 6/2021 | Millet | |
| 11,103,470 B2 | 8/2021 | Millet | |
| 11,129,802 B2 | 9/2021 | Millet | |
| 11,173,138 B2 * | 11/2021 | Lowery | A61P 43/00 |
| 11,185,518 B2 | 11/2021 | Millet | |
| 11,202,769 B2 | 12/2021 | Millet | |
| 11,241,403 B2 | 2/2022 | Millet | |
| 11,690,817 B2 | 7/2023 | Millet | |
| 11,793,778 B2 | 10/2023 | Millet | |
| 11,806,324 B2 | 11/2023 | Millet | |
| 11,944,598 B2 | 4/2024 | Millet | |
| 11,950,616 B2 | 4/2024 | Millet | |
| 11,969,411 B2 | 4/2024 | Lowery et al. | |
| 12,186,297 B2 | 1/2025 | Millet | |
| 12,251,362 B2 | 3/2025 | Lowery et al. | |
| 12,350,243 B2 * | 7/2025 | Millet | A61K 31/19 |
| 2001/0014696 A1 | 8/2001 | Veech | |
| 2001/0018866 A1 | 9/2001 | Fischer | |
| 2001/0041736 A1 | 11/2001 | Veech | |
| 2002/0013339 A1 | 1/2002 | Martin et al. | |
| 2002/0124370 A1 | 9/2002 | Deckert et al. | |
| 2003/0022937 A1 | 1/2003 | Veech | |
| 2004/0126366 A1 | 7/2004 | Kaddurah-Daouk et al. | |
| 2004/0138293 A1 | 7/2004 | Werner et al. | |
| 2004/0266872 A1 | 12/2004 | Veech | |
| 2005/0129783 A1 | 6/2005 | McCleary et al. | |
| 2005/0169968 A1 | 8/2005 | Elmaleh et al. | |
| 2006/0165777 A1 | 7/2006 | Solomon et al. | |
| 2006/0275253 A1 | 12/2006 | Ushida et al. | |
| 2007/0029913 A1 | 2/2007 | Chen | |
| 2007/0135376 A1 | 6/2007 | Henderson | |
| 2007/0179197 A1 | 8/2007 | Henderson | |
| 2008/0058416 A1 | 3/2008 | Greenwood et al. | |
| 2008/0287372 A1 | 11/2008 | Henderson | |
| 2009/0131475 A1 | 5/2009 | Uesugi et al. | |
| 2009/0253781 A1 | 10/2009 | Veech | |
| 2009/0306221 A1 | 12/2009 | Guy et al. | |
| 2009/0325984 A1 | 12/2009 | Costentin et al. | |
| 2010/0041751 A1 | 2/2010 | Henderson | |
| 2010/0056631 A1 | 3/2010 | Hisamura et al. | |
| 2010/0113494 A1 | 5/2010 | Hu et al. | |
| 2010/0197758 A1 | 8/2010 | Andrews et al. | |
| 2010/0210726 A1 | 8/2010 | Kuriyama | |
| 2010/0298294 A1 | 11/2010 | Clarke et al. | |
| 2011/0111049 A1 | 5/2011 | Andrews et al. | |
| 2011/0237666 A1 | 9/2011 | Clarke et al. | |
| 2011/0287114 A1 | 11/2011 | Johnson | |
| 2012/0053240 A1 | 3/2012 | Rathmacher et al. | |
| 2012/0071548 A1 | 3/2012 | Veech | |
| 2012/0171165 A1 | 7/2012 | Buck et al. | |
| 2012/0202891 A1 | 8/2012 | Stinchcomb et al. | |
| 2013/0079406 A1 | 3/2013 | Veech | |
| 2013/0337116 A1 | 12/2013 | Petralia | |
| 2014/0256808 A1 | 9/2014 | Henderson | |
| 2014/0329893 A1 | 11/2014 | Veech | |
| 2014/0350105 A1 | 11/2014 | D'Agostino et al. | |
| 2014/0352728 A1 | 12/2014 | Svensson | |
| 2015/0018415 A1 | 1/2015 | Veech | |
| 2015/0063140 A1 | 3/2015 | Yi et al. | |
| 2015/0065571 A1 | 3/2015 | Clarke et al. | |
| 2015/0132280 A1 | 5/2015 | Lopez et al. | |
| 2015/0144074 A1 | 5/2015 | Fujimoto et al. | |
| 2015/0320809 A1 | 11/2015 | Carpenter et al. | |
| 2015/0363750 A1 | 12/2015 | Svensson et al. | |
| 2016/0067207 A1 | 3/2016 | D'Agostino et al. | |
| 2016/0193173 A1 | 7/2016 | Clarke et al. | |
| 2016/0256411 A1 | 9/2016 | Aung-Din | |
| 2016/0263071 A1 | 9/2016 | Borges et al. | |
| 2016/0272603 A1 | 9/2016 | Kravchenko et al. | |
| 2017/0020844 A1 | 1/2017 | Galinski | |
| 2017/0029650 A1 | 2/2017 | Veling et al. | |
| 2017/0172969 A1 | 6/2017 | D'Agostino et al. | |
| 2017/0258745 A1 | 9/2017 | Millet | |
| 2017/0266148 A1 | 9/2017 | D'Agostino et al. | |
| 2017/0290792 A1 | 10/2017 | Cavaleri | |
| 2017/0296501 A1 | 10/2017 | Lowery et al. | |
| 2017/0296520 A1 | 10/2017 | Lowery et al. | |
| 2017/0298339 A1 | 10/2017 | Hanson et al. | |
| 2017/0304564 A1 | 10/2017 | Dehaan et al. | |
| 2018/0020699 A1 | 1/2018 | Steup | |
| 2018/0021274 A1 | 1/2018 | Arnold | |
| 2018/0021281 A1 | 1/2018 | Berger | |
| 2018/0055797 A1 | 3/2018 | Llosa et al. | |
| 2018/0057846 A1 | 3/2018 | Llosa et al. | |
| 2018/0195096 A1 | 7/2018 | Veech et al. | |
| 2018/0214399 A1 | 8/2018 | Spector et al. | |
| 2018/0238586 A1 | 8/2018 | Sugatani et al. | |
| 2019/0099394 A1 | 4/2019 | Ari et al. | |
| 2019/0151267 A1 | 5/2019 | Millet | |
| 2019/0167613 A1 | 6/2019 | Millet | |
| 2019/0167614 A1 | 6/2019 | Millet | |
| 2019/0177673 A1 | 6/2019 | Llosa et al. | |
| 2019/0183220 A1 | 6/2019 | Takada | |
| 2019/0183820 A1 | 6/2019 | Millet | |
| 2019/0183821 A1 | 6/2019 | Millet | |
| 2019/0191755 A1 | 6/2019 | Garvey et al. | |
| 2019/0209501 A1 | 7/2019 | Tinsley, M et al. | |
| 2019/0255028 A1 | 8/2019 | Lowery et al. | |
| 2019/0262293 A1 | 8/2019 | Millet | |

(56) References Cited

U.S. PATENT DOCUMENTS

| | | | |
|---|---|---|---|
| 2019/0313682 A1 | 10/2019 | Nagel | |
| 2019/0321309 A1 | 10/2019 | Millet | |
| 2020/0030266 A1 | 1/2020 | Bradley et al. | |
| 2020/0061004 A1 | 2/2020 | Millet | |
| 2020/0078973 A1 | 3/2020 | Valeze et al. | |
| 2020/0129463 A1 | 4/2020 | Lowery et al. | |
| 2020/0140371 A1 | 5/2020 | Verdin et al. | |
| 2020/0170982 A1 | 6/2020 | Millet | |
| 2020/0253909 A1 | 8/2020 | Millet | |
| 2020/0268701 A1 | 8/2020 | D'Agostino et al. | |
| 2020/0276203 A1 | 9/2020 | Larocca et al. | |
| 2021/0095867 A1 | 4/2021 | Gururaja et al. | |
| 2021/0106168 A1 | 4/2021 | Cingolani et al. | |
| 2021/0205241 A1 | 7/2021 | Millet | |
| 2021/0393560 A1 | 12/2021 | Lowery et al. | |
| 2022/0133673 A1 | 5/2022 | Millet | |
| 2022/0202760 A1 | 6/2022 | Greenwood et al. | |
| 2023/0072854 A1 | 3/2023 | Purpura et al. | |
| 2023/0115966 A1 | 4/2023 | Wells et al. | |
| 2023/0201145 A1 | 6/2023 | Millet | |
| 2023/0346721 A1 | 11/2023 | Millet | |
| 2024/0024265 A1 | 1/2024 | Millet | |
| 2024/0197668 A1 | 6/2024 | Millet | |
| 2025/0025434 A1 | 1/2025 | Millet | |

FOREIGN PATENT DOCUMENTS

| | | | |
|---|---|---|---|
| CN | 1256629 A | 6/2000 | |
| CN | 1347319 A | 5/2002 | |
| CN | 1104978 C | 4/2003 | |
| CN | 1184978 C | 1/2005 | |
| CN | 1972698 A | 5/2007 | |
| CN | 101674730 A | 3/2010 | |
| CN | 101678043 A | 3/2010 | |
| CN | 101969769 A | 2/2011 | |
| CN | 102164884 A | 8/2011 | |
| CN | 104224823 A | 12/2014 | |
| CN | 105050594 A | 11/2015 | |
| CN | 106038532 A | 10/2016 | |
| CN | 106459646 A | 2/2017 | |
| CN | 106858066 A | 6/2017 | |
| CN | 108253621 A | 7/2018 | |
| CN | 109480284 A | 3/2019 | |
| CN | 111655244 A | 9/2020 | |
| CN | 111867576 A | 10/2020 | |
| CN | 112262936 A | 1/2021 | |
| DE | 102017210992 A1 | 1/2019 | |
| EP | 0008700 A1 | 3/1980 | |
| EP | 1112711 A1 | 7/2001 | |
| EP | 1178748 A1 | 2/2002 | |
| EP | 1827412 A1 | 9/2007 | |
| EP | 1915144 A2 | 4/2008 | |
| EP | 2283834 A2 | 2/2011 | |
| EP | 1755743 B1 | 4/2013 | |
| EP | 2976073 A1 | 1/2016 | |
| EP | 3094321 A1 | 11/2016 | |
| EP | 3366173 A2 | 8/2018 | |
| EP | 3446045 A1 | 2/2019 | |
| FR | 2997302 A1 | 5/2014 | |
| GB | 2391493 A | 2/2004 | |
| ID | 201701176 | 2/2017 | |
| JP | 11-060434 A | 3/1999 | |
| JP | 2002-521330 A | 7/2002 | |
| JP | 2004-035417 A | 2/2004 | |
| JP | 2008-127369 A | 6/2008 | |
| JP | 5030553 B2 | 9/2012 | |
| JP | 2015-042644 A | 3/2015 | |
| JP | 5690261 B2 | 3/2015 | |
| JP | 2015-514104 A | 5/2015 | |
| JP | 2015-102323 A | 6/2015 | |
| JP | 2016-514725 A | 5/2016 | |
| JP | 2016-121128 A | 7/2016 | |
| JP | 2017-046688 A | 3/2017 | |
| JP | 2018-158897 A | 10/2018 | |
| JP | 2018-158898 A | 10/2018 | |

| | | | |
|---|---|---|---|
| JP | 2018-158899 A | 10/2018 | |
| JP | 2019-533010 A | 11/2019 | |
| JP | 2020-502652 A | 1/2020 | |
| JP | 2020-527583 A | 9/2020 | |
| JP | 2021-504476 A | 2/2021 | |
| JP | 2021-506294 A | 2/2021 | |
| JP | 2021-127322 A | 9/2021 | |
| JP | 2021-193945 A | 12/2021 | |
| RU | 2345546 C2 | 2/2009 | |
| WO | 87/03808 A1 | 7/1987 | |
| WO | 98/41200 A1 | 9/1998 | |
| WO | 00/04895 A2 | 2/2000 | |
| WO | 00/15216 A1 | 3/2000 | |
| WO | 00/69315 A1 | 11/2000 | |
| WO | 03/70823 A2 | 8/2003 | |
| WO | 2004108740 A1 | 12/2004 | |
| WO | 2005/077348 A1 | 8/2005 | |
| WO | 2005/107724 A1 | 11/2005 | |
| WO | 2006/029577 A1 | 3/2006 | |
| WO | 2006/061624 A1 | 6/2006 | |
| WO | 2007/115282 A2 | 10/2007 | |
| WO | 2007/138322 A1 | 12/2007 | |
| WO | 2008/005818 A1 | 1/2008 | |
| WO | 2008/021394 A2 | 2/2008 | |
| WO | 2008/024408 A2 | 2/2008 | |
| WO | 2009/089144 A1 | 7/2009 | |
| WO | 2010/021766 A1 | 2/2010 | |
| WO | 2010/104595 A1 | 9/2010 | |
| WO | 2011/101171 A1 | 8/2011 | |
| WO | 2012/019295 A1 | 2/2012 | |
| WO | 2012/024611 A1 | 2/2012 | |
| WO | 2013/057506 A1 | 4/2013 | |
| WO | 2013/150153 A1 | 10/2013 | |
| WO | 2014/153415 A2 | 9/2014 | |
| WO | 2014/153416 A1 | 9/2014 | |
| WO | 2015/063140 A1 | 5/2015 | |
| WO | 2015/071811 A1 | 5/2015 | |
| WO | 2015/156865 A1 | 10/2015 | |
| WO | 2016/123229 A1 | 8/2016 | |
| WO | 2016/149687 A1 | 9/2016 | |
| WO | 2017/156446 A1 | 9/2017 | |
| WO | 2017/165443 A1 | 9/2017 | |
| WO | 2017/165445 A1 | 9/2017 | |
| WO | 2017/182664 A1 | 10/2017 | |
| WO | 2017/184788 A1 | 10/2017 | |
| WO | 2017/208217 A2 | 12/2017 | |
| WO | 2018/055388 A1 | 3/2018 | |
| WO | 2018/089863 A1 | 5/2018 | |
| WO | 2018/114309 A1 | 6/2018 | |
| WO | 2018/132189 A1 | 7/2018 | |
| WO | 2018/175879 A1 | 9/2018 | |
| WO | 2018/187324 A1 | 10/2018 | |
| WO | 2018/187852 A1 | 10/2018 | |
| WO | 2019/018683 A1 | 1/2019 | |
| WO | 2019/099531 A1 | 5/2019 | |
| WO | 2019/104082 A1 | 5/2019 | |
| WO | 2019/108683 A1 | 6/2019 | |
| WO | 2019/118624 A1 | 6/2019 | |
| WO | 2019/200132 A1 | 10/2019 | |
| WO | 2019/204148 A1 | 10/2019 | |
| WO | 2019/237152 A1 | 12/2019 | |
| WO | 2019/237185 A1 | 12/2019 | |
| WO | 2020/041871 A1 | 3/2020 | |
| WO | 2020/092451 A1 | 5/2020 | |
| WO | 2020/257055 A1 | 12/2020 | |
| WO | 2021/178547 A1 | 9/2021 | |
| WO | 2022/040644 A2 | 2/2022 | |
| WO | 2022/232469 A1 | 11/2022 | |

OTHER PUBLICATIONS

Krotkiewski, "Value of VLCD Supplementation with Medium Chain Triglycerides", Int J Obes Relat Metab Disord, Sep. 2001, 25 (9), pp. 1393-1400.

Lang Chaochun, "Healthy fitness and exercise prescription", Nov. 30, 2013, p. 201.

(56) References Cited

OTHER PUBLICATIONS

Lannotti et al., "Effects of non-euphoric plant cannabinoids on muscle quality and performance of dystrophic mdx mice", Br J Pharmacol, May 2019, vol. 176, No. 10, pp. 1568-1584.

Lee, S. et al. Strategic Approaches for Colon Targeted Drug Delivery: An Overview of Recent Advancements, 2020, Pharmaceutics, 12(68): 1-20 (Year: 2020).

Lile et al. Drug Alcohol Depend. 2012, 122 (1-2), 61-69.

Lincoln et al. Archives of Biochemistry and Biophysics 1987, 259 (1), 149-156.

Lonza, Duocap Capsules, Feb. 16, 2018, https ://web .archive .org/web/20180216001656/https://www.capsugel.com/consumer-health-nutrition-products/duocap-capsules (Year: 2018).

Luis Villasenor, "Supplements and Ketogenic Diets—Facts and Myths", Retrieved from https://www.ketogains.com/2015/09/supplements-and-ketogenic-diets-facts-and-myths/, Sep. 18, 2015, pp. 15.

Lytra. G. et al., "Distribution and Organoleptic Impact of Ethyl 3-Hydroxybutanoate Enantiomers in Wine," J. Agric. Food Chem, vol. 63, Issue 48, 2015, pp. 10484-10491.

Maalouf Met al., "Ketones inhibit mitochondrial production of reactive oxygen species production following glutamate excitotoxicity by increasing NADH oxidation," Neuroscience, New York, NY, US, vol. 145, Issue 1, Mar. 2, 2007, pp. 256-264.

Maalouf Met al., "The neuroprotective properties of calorie restriction, the ketogenic diet, and ketone bodies," Brain Research Reviews, Elsevier, NL, vol. 59, No. 2, Mar. 1, 2009, pp. 293-315.

Maguire et al., "Gut dysbiosis, leaky gut, and intestinal epithelial proliferation in neurological disorders: towards the development of a new therapeutic using amino acids, prebiotics, probiotics, and postbiotics", Rev Neurosci . Jan. 28, 2019, vol. 30, No. 2, pp. 179-201.

Malo, M. S. et al., Intestinal alkaline phosphatase preserves the normal homeostasis of gut microbiota, 2010, Gut, 59, 1476-1484 (Year: 2010).

Mangels D.R. et al., "Catechins as Potential Mediators of Cardiovascular Health", Translational Sciences, vol. 37, No. 5, May 1, 2017, pp. 757-763.

Maroni, A. et al. Enteric coatings for colonic drug delivery: state of the art, 2017, Expert Opinion on Drug Delivery, 14 (9): 1027-1029 (Year: 2017).

McFarland, L. Use of probiotics to correct dysbiosis of normal microbiota following disease or disruptive events: a systematic review, 2014, BMJ Open, 4(8): 1-18 (Year: 2014).

Murray, Andrew J., et al. "Novel ketone diet enhances physical and cognitive performance", The FASEB Journal, No. Dec. 30, 2016.

National Center for Biotechnology Information. PubChem Compound Summary for CID 441, 3-Hydroxybutyric acid, https://pubchem.ncbi.nlm.nih.gov/compound/3-Hydroxybutyric-acid. (Year: 2005).

Newman et al. "B-Hydroxybutyrate: A Signaling Metabolite", Annu Rev Nutr., Aug. 21, 2017, pp. 1-30.

Newman et al., "B-hydroxybutyrate: Much more than a metabolite", Diabetes Res Clin Pract., Nov. 2014.

Non-Final Rejection Mailed on Sep. 9, 2020 for U.S. Appl. No. 16/783,956.

Nova Max Plus Glucose and Ketone Testing with One Monitor. Downloaded Apr. 1, 2015. http://www.novacares.com/nova-max-plus/.

O'Mailey et al., Appl. Physiol. Nutr. Metab. 42: 1031-1035 (2017) Published at www.NRCRESEARCHPRESS.com/ APNM on Jul. 27, 2017.

O'Meara, Cyndi, Changing Habits, Ketosis—Can we achieve it in a pill?, https://changinghabits. com.au/ketosis-can- we-achieve-it-in-a-pill/, 12 pages, (Jan. 13, 2017).

Office Action received for European Patent Application No. 17786592. 0, mailed on Jun. 17, 2022, 7 pages.

Office Action received for European Patent Application No. 17786592. 0, mailed on Sep. 25, 2020, 7 pages.

Office Action received for European Patent Application No. 19788264. 0, mailed on Mar. 13, 2024, 5 pages.

Office Action received for European Patent Application No. 19880284. 5, mailed on Nov. 9, 2023, 5 pages.

Office Action received for European Patent Application No. 20805593. 9, mailed on Dec. 22, 2023, 7 pages.

Paraxanthine-Pubchem—2023 (Year: 2023).

Parker, Steve, "Ketogenic Mediterraanean Diet: Version 2.3," Nov. 23, 2010, pp. 1-3. (Year: 2010).

Partial supplementary European search report (EPO Form 1507US) issued by the European Patent Office on Sep. 21, 2016 for corresponding European Application No. 14770025.6.

Patel, R. et al. Therapeutic Use of Prebiotics, Probiotics, and Postbiotics to Prevent Necrotizing Enterocolitis: What is the Current Evidence? 2014, Clinics in Perinatology, 40(1): 11-25 (Year: 2014).

Pete J Cox et al., "Acute nutritional ketosis: implications for exercise performance and metabolism," Extreme Physiology & Medicine, vol. 3, Issue 1, Dec. 1, 2014, pp. 1-9.

Precision Xtra vs. NovaMax Plus: Ketone Meter Evaluation. Jimmy Moore's Livin' La Vida Low Garb Blog. Downloaded Apr. 1, 2015. http://livinlavidalowcarb.com/blog/precision-xtra-vs-novamax-plus-ketone-meter-evaluation/15918.

Pubchem, "Acetoacetic acid" Electronic Resource: https://pubchem. ncbi.nim.nih.gov/compound/Acetoacetic-acid, Retrieved on Sep. 3, 2019.

Rho et al. "Acetoacetate, Acetone, and Dibenzylamine (A Contaminant In L-(+)-Beta-Hydroxybutyrate) Exhibit Direct Anticonvulsant Actions In Vivo", Epilepsia, Raven Press Ltd, New York, US, vol. 43, No. 4, Apr. 1, 2002 (Apr. 1, 2002), pp. 358-361.

Riccio et al. The human gut microbiota is neither an organ nor a commensal, 2020, FEBS Letters, 594(20): 3262-3271 (Year: 2020).

Rich A.J., "Ketone Bodies as Substrates," Proceedings of the Nutrition Society (1990), vol. 49, 361-373.

Robson et al. Expert Opin. Drug Saf. (2011), vol. 10, pp. 675-685 (Year: 2011).

Roeder, Lois M., et al. The Effects of Ketone Bodies, Bicarbonate, and Calcium on Hepatic Mitochondrial Ketogenesis. Archives of Biochemistry and Biophysics, vol. 217, No. 2, Sep. pp. 460-467, 1982.

Rogers GB et al. From gut dysbiosis to altered brain function and mental illness: mechanisms and pathways, 2016, Molecular Psychiatry, 21: 738-748 (Year: 2016).

Sajewicz et al. In Journal of Liquid Chromatography & Related Technologies, 33:1047-1057 (2010) (Year: 2010).

Sanchez, J. I. et al. Arabinoxylan-oligosaccharides (AXOS) affect the protein/carbohydrate fermentation balance and microbial population dynamics of the Simulator of Human Intestinal Microbial Ecosystem, 2009, Microbial Biotechnology, 2(1): 101-113 (Year: 2009).

Sara, How do you know which product is right for you? How to choose exogenous ketones, https://ketosupplements.co.uk/how-to-choose-exogenous-ketones/, 10 pages, (Sep. 25, 2017).

Search Report and Written Opinion issued by the Intellectual Property Office of Singapore on Apr. 18, 2016 for corresponding Singapore Application No. 11201506780R.

Serum Ketones Test. MedlinePlus Medical Encyclopedia. Downloaded Apr. 1, 2015. http://www.nlm.nih.gov/medlineplus/ency/article/003498.htm.

A New Toy Measuring Blood Ketones. Diet Doctor, Aug. 21, 2012. Dowloaded Apr. 1, 2015. http://www.dietdoctor.com/a-new-toy-measuring-blood-ketoones.

Allendorfer et al., "Neuroimaging studies towards understanding the central effects of pharmacological cannabis products on patients with epilepsy", Epilepsy Behav, May 2017, vol. 70, pp. 349-354.

Amazon, "Perfect Keto Perform Pre Workout Powder—Bum Fat for Fuel Energy Supplement Drink Mix for Men and Women—Keto Friendly with Ketone Salts, BCAA, Nitric Oxide & MCT", Sep. 25, 2017 entire document especially p. 1 Retrieved from https://www. amazon.com/Perfect-Keto-Perform-PreworkoutSupplement/dp/ B0751379Q9/ref=sr_1_9?dchild= 1 &keywords=ketone+pre+workout &qid= 1597938465&sr=8-9.

(56) References Cited

OTHER PUBLICATIONS

Anonymous: "Strawberry Pineapple Flavour Pre-Exertion Performance Optimizer", MINTEL, Database accession No. 5661617, 2018, pp. 4.

Arendash et al. "Caffeine and Coffee as Therapeutics Against Alzheimer's Disease", Journal of Alzheimer's Disease 20, 2010, S117-S126.

Arnold, Instant Ketosis?, (2013), Aug. 4, 2013 (retrieved on Apr. 21, 2017), p. 1-3. Retrieved from the internet; URL: <http://patrickarnoldblog.com/instant-ketosis/. (Year: 2013).

Bala et al. Drug Invention Today. Jun. 1, 2018;10(6), 929-931.

Bastin et al., "Salt Slection and Optimisation Procedures for Pharmaceutical New Chemical Entities", American Chemical Society and The Royal Society of Chemistry, vol. 4, No. 5, 2000, pp. 427-435.

Blazquez et al. Journal of Neurochemistry, 1999, vol. 72 No. 4, pp. 1759-1768. (Year: 1999).

Budin. N. et al., "Efficient synthesis of the ketone body ester (R)-3-hydroxybutyryl-(R)-3-hydroxybutyrate and its (S, S) enantiomer," Bioorganic Chemistry, vol. 80, Oct. 2018, pp. 560-564.

Clarke, et al., Kinetics, safety and tolerability of (R)-3-hydroxybutyl (R)-3-hydroxybutyrate in healthy adult subjects. Regul Toxicol Pharmacol. Aug. 2012; 63(3):401-8.

Craciun, S. et al. Microbial conversion of choline to trimethylamine requires a glycyl radical enzyme, 2012, PNAS, 109(52): 21307-21312 (Year: 2012).

Cresci, G. et al., Lactobacillus GG and Tributyrin Supplementation Reduce Antibiotic-Induced Intestinal Injury, 2013, Journal of Parenteral and Enteral Nutrition, 37(6), 1-20 (Year: 2013).

D'Souza et al. Neuropsychopharmacology 2004, 29, 1558-1572.

Daniells, Stephen, 'This is caffeine-evolved': Ingenious Ingredients co-founder talks up potential of paraxanthine,' Nov. 3, 2021, 2 pages, retrieved from https://www.nutraingredients-usa.com/Article/2021/11/03/This-is-caffeine-evolved-Ingenious-Ingredients-co-founder-talks-up-potential-of-paraxanthine accessed Feb. 7, 2023.

Database GNPD Mintel, Sep. 29, 2016, anonymous, "Blue Lemon Ice Advanced Formula", XP093048090, Database accession No. 4315637, pp. 3.

Decision to grant received for European Patent Application No. 17786592.0, mailed on Nov. 3, 2023, 2 pages.

Dedkova et al. "Role of B-hydroxybutyrate, its polymer poly-b-hydroxybutyrate and inorganic polyphosphate in mammalian health and disease", Frontiers in Physiology, Jul. 17, 2014, pp. 1-22.

Dietary Guidelines Recommendations at https://health.gov/our-work/food-nutrition/2015-2020-dietary-guidelines/ guidelines/ appendix-7/ (2010) (retrieved from the internet Oct. 20, 2020) (Year: 2010).

Dolson, Laura. How to Test Your Blood for Ketones. Downloaded Apr. 1, 2015. http://lowcarbdiets.about.com/od/KetogenicDiets/a/How-to-Test-Blood-For-Ketones.htm.

Energy Times—"Herbal Keto Support", Jan. 15, 2008 (5 pages).

English translation of WO2013057506 accessed form patentscope. wipo.com Jul. 14, 2021.

Enhancing Human Performance: Ketones. Blue Sky Fact Finding Meeting, Oct. 24, 2012.

European Search Report received for EP Patent Application No. 19880284.5, mailed on Jul. 12, 2022, 11 pages.

European Search Report received for EP Patent Application No. 20755289.4, mailed on Oct. 11, 2022, 7 pages.

European Search Report received for EP Patent Application No. 20755994.9, mailed on Sep. 21, 2022, 6 pages.

European Search Report received for EP Patent Application No. 20805593.9, mailed on Dec. 16, 2022, 9 pages.

European Search Report received for EP Patent Application No. 21750261.6, mailed on Feb. 2, 2024, 10 pages.

European Search Report received for EP Patent Application No. 21862356.9, mailed on Jul. 1, 2024, 10 pages.

Extended European Search Report issued in PCT/US2017021886 dated Oct. 17, 2019.

Extended European Search Report pursuant to Rule 62 EPC (EPO Form 1507S) issued on Jan. 24, 2017 for corresponding European Patent Application No. 14770025.6.

Extended European Search Report received for EP Patent Application No. 19788264.0, mailed on Dec. 20, 2021, 11 pages.

Extended European Search Report received for EP Patent Application No. 20755770.3, mailed on Sep. 1, 2022, 7 pages.

First Examination Report for New Zealand Patent Application No. 711433 issued by the New Zealand Intellectual Property Office dated Mar. 10, 2016.

First Office Action issued by the Chinese State Intellectual Property Office on Nov. 4, 2016 for corresponding Chinese Patent Application No. 201480016818.0.

Grootaert, C. Comparison of prebiotic effects of arabinoxylan oligosaccharides and inulin in a simulator of the human intestinal microbial ecosystem, 2009, FEMS Microbiology Ecology, 69: 231-242 (Year: 2009).

Haces M L et al: "Antioxidant capacity contributes to protection of ketone bodies against oxidative damage induced during hypoglycemic conditions", Experimental Neurology, Elsevier, Amsterdam, NL, vol. 211, No. 1, May 1, 2008 (May 1, 2008), pp. 85-96.

Hashim, Sami A., et al., "Ketone body therapy: from the ketogenic diet to the oral administration of ketone ester", Journal of Lipid Research, vol. 55, 2014.

Haywood A, Glass BD. Pharmaceutical excipients—where do we begin? Australian Prescriber. 2011; 34: 112-114.

Henderson, Samuel T. "Ketone Bodies as a Therapeutic for Alzheimer's Disease." Neurotherapeutics. Jul. 2008; 5(3):470-80.

Holscher, H. Dietary fiber and prebiotics and the gastrointestinal microbiota, 2017, Gut Microbes, 8(2): 172-184 (Year: 2017).

Holtzman et al., "Role of adenosine receptors in caffeine tolerance", J. Pharmacol. Exp. Ther., 1991 ; 256(1 ):62-68.

Huang Dexiang et al., "Clinical Intravenous Nutrition", Shanghai Medical University Press Jan. 31, 1994, pp. 121-124.

Ichim, T. et al., Experimental support for the effects of a probiotic/digestive enzyme supplement on serum cholesterol concentrations and the intestinal microbiome, 2016, Journal of Translational Medicine, 14(184), 1-9 (Year 2016).

Intention to grant received for European Patent Application No. 17786592.0, mailed on Jun. 27, 2023, 7 pages.

International Preliminary Report on Patentability received for PCT Patent Application No. PCT/US17/28465, mailed on Nov. 1, 2018, 7 pages.

International Preliminary Report on Patentability received for PCT Patent Application No. PCT/US17/28466, mailed on Nov. 1, 2018, 8 pages.

International Preliminary Report on Patentability received for PCT Patent Application No. PCT/US19/58676, mailed on May 14, 2021, 6 pages.

International Preliminary Report on Patentability received for PCT Patent Application No. PCT/US20/37289, mailed on Dec. 30, 2021, 6 pages.

International Preliminary Report on Patentability received for PCT Patent Application No. PCT/US2014/031237, mailed on Oct. 1, 2015, 8 pages.

Shigeno et al. in Biosci. Biotech. Biochem., 56(2), 320-323 (1992) (Year: 1992).

Short, Jay, Effects of A Ketone/Caffeine Supplement On Cycling and Cognitive Performance, Master's thesis, Ohio State University, 61 pages, (Jan. 1, 2017).

Slavin, J. Fiber and Prebiotics: Mechanisms and Health Benefits, 2013, Nutrients, 5: 1417-1425 (Year: 2013).

Sorensen et al. ("Simultaneous determination of B-hydroxybutyrate and B-hydroxy-B-methylbutyrate in human whole blood using hydrophilic interaction liquid chromatography electrospray tandem mass spectrometry", Clinical Biochemistry, 2013, vol. 46, pp. 1877-1883) (Year: 2013).

Stefan et al., "The Effects of Exogenous Beta-Hydroxybutyrate Supplementation on Metrics of Safety and Health", International Journal of Nutrition and Food Sciences, vol. 9, No. 6, Nov. 2020, pp. 154-162.

Stubbs et al., "On the Metabolism of Exogenous Ketones in Humans", frontiers in Physiology, vol. 8, 2017, 13 pages.

(56) References Cited

OTHER PUBLICATIONS

Supplementary European Search Report received for EP Patent Application No. 17786592.0, mailed on Nov. 25, 2019, 10 pages.

Tanaka, J., et al., "Significance of Blood Ketone Body Ration as an indicator of Hepatic Cellular Energy Status in Jaundiced Rabbits", Gastroenterology, 1979, vol. 76, No. 4, pp. 691-696.

The Medical Republic, 2018, Sustained Release Sodium Butyrate Supplement Now Available to Support Management of GI Disorders, https://medicalrepublic.com.au/ sustained-release-sodium-butyrate-supplement-now-available-support-management-gi-disorders/15791; newly cited (Year: 2018).

Tisdale, "Reduction of weight loss and tumour size in a cachexia model by a high fat diet", British Journal of Cancer, Jul. 1987, vol. 56, p. 39-43.

Tsai et al., "Stereoselective effects of 3-hydroxybutyrate on glucose utilization of rat cardiomyocytes" life Sciences 78 (2006) pp. 1385-1391.

U.S. Appl. No. 62/324,798, filed Apr. 19, 2016, Lowery, priority document to U.S. Pat. No. 11,173,138.

Vandenberghe et al., "Caffeine intake increases plasma ketones: an acute metabolic study in humans", Canadian Journal of Physiology and Pharmacology, vol. 95, 2017, pp. 455-458.

Veech, "The Therapeutic Implications of Ketone Bodies: The Effects of Ketone Bodies in Pathological Conditions: Ketosis, Ketogenic Diet, Redox States, Insulin Resistance, and Mitochondrial Metabolism", Prostaglandins Leukot Essent Fatty Acids, Mar. 2004, 70(3), pp. 309-319.

Veech, et al., "Ketone Bodies Mimic the Life Span Extending Properties of Caloric Restriction", IUBMB Life Feb. 8, 2017.

Vorgerd, M. And J. Zange. Treatment of glycogenosys type V (McArdle disease) with creatine and ketogenic diet with clinical scores and with 31P-MRS on working leg muscle. Acta Myologica, 2007; XXVI; pp. 61-63.

Walton, G. et al. A randomised, double-blind, placebo controlled cross-over study to determine the gastrointestinal effects of consumption of arabinoxylan-oligosaccharides enriched bread in healthy volunteers, 2012, Nutrition Journal, 11(36): 1-11 (Year: 2012).

Wang et al. Eucommiae cortex polysaccharides attenuate gut microbiota dysbiosis and neuroinflammation in mice exposed to chronic unpredictable mild stress: Beneficial in ameliorating depressive-like behaviors, 2024, Journal of Affective Disorders, 334: 278-292 (Year: 2024).

Williams et al., "The Chemistry of the Ketogenic Diet: Updates and Opportunities in Organic Synthesis", Int J Mol Sci., May 15, 2021, vol. 22, No. 10, 5230, pp. 1-18.

WO2009045481, Pan et al. Published Apr. 9, 2009 Listed in this section as citation type "foreign" does not allow for any appropriate country code for "WO" documents.

Wu et al., "Medium-Chain Triglycerides in Infant Formulas and Their Relation to Plasma Ketone Body Concentrations," Pediatric Research, vol. 20, No. 4, (1986), pp. 338-341.

Yang Y. et al., Role of Adherent-Invasive *Escherichia coli* in Inflammatory Bowl Disease, Letters in Biotechnology, No. 06, Nov. 30, 2016.

Yang Yue et al., "Research on sarcopenic obesity", Chinese Journal of Modern Medicine, vol. 20, No. 3, Mar. 25, 2018, pp. 98-101.

Yang Zeyi, "Biochemistry of sports nutrition scientific research progress", Mar. 31, 2004, vol. 23, No. 2, pp. 158-165.

Zaleski, A. et al., Butyric acid in irritable bowel syndrome, 2013, Prz Gastroenterol, 8(6), 350-353 (Year: 2013).

Zare et al., "Wake-Promoting Agents, Insights into Clinical Use and Molecular Perspectives," Journal of Advanced Medical Sciences and Applied Technologies (JAMSAT), vol. 2, 2016, pp. 129-140.

Zeng Jing et al., "B-hydroxy-3-methyl—The clinical effects and mechanism", vol. 2, No. 2, Jun. 9, 2015, pp. 57-62.

International Preliminary Report on Patentability received for PCT Patent Application No. PCT/US2017/021886, mailed on Sep. 20, 2018, 9 pages.

International Preliminary Report on Patentability received for PCT Patent Application No. PCT/US2018/062093, mailed on Jun. 4, 2020, 6 pages.

International Preliminary Report on Patentability received for PCT Patent Application No. PCT/US2018/062096, mailed on Jul. 2, 2020, 8 pages.

International Preliminary Report on Patentability received for PCT Patent Application No. PCT/US2019/027214, mailed on Oct. 29, 2020, 09 pages.

International Preliminary Report on Patentability received for PCT Patent Application No. PCT/US2019/048357, mailed on Mar. 11, 2021, 08 pages.

International Preliminary Report on Patentability received for PCT Patent Application No. PCT/US2019/048364, mailed on Mar. 11, 2021, 7 pages.

International Preliminary Report on Patentability received for PCT Patent Application No. PCT/US2020/016952, mailed on Aug. 26, 2021, 7 pages.

International Preliminary Report on Patentability received for PCT Patent Application No. PCT/US2020/017552, mailed on Aug. 26, 2021, 7 pages.

International Preliminary Report on Patentability received for PCT Patent Application No. PCT/US2020/017555, mailed on Aug. 26, 2021, 7 pages.

International Preliminary Report on Patentability received for PCT Patent Application No. PCT/US2020/017556, mailed on Aug. 26, 2021, 7 pages.

International Preliminary Report on Patentability received for PCT Patent Application No. PCT/US2020/033159, mailed on Nov. 25, 2021, 6 pages.

International Preliminary Report on Patentability received for PCT Patent Application No. PCT/US2021/017078, mailed on Aug. 18, 2022, 7 pages.

International Preliminary Report on Patentability received for PCT Patent Application No. PCT/US2021/045186, mailed on Mar. 9, 2023, 7 pages.

International Preliminary Report on Patentability received for PCT Patent Application No. PCT/US2021/050302, mailed on Mar. 2, 2023, 8 pages.

International Preliminary Report on Patentability received for PCT Patent Application No. PCT/US2021/063559, mailed on Jul. 6, 2023, 6 pages.

International Preliminary Report on Patentability received for PCT Patent Application No. PCT/US2023/020407, mailed on Nov. 7, 2024, 7 pages.

International Preliminary Report on Patentability received for PCT Patent Application No. PCT/US2023/020417, mailed on Nov. 7, 2024, 8 pages.

International Search Report and Written Opinion for PCT/US17/2846 dated Jul. 5, 2017 (9 pages).

International Search Report and Written Opinion issued in PCT/US19/48364 dated Nov. 15, 2019.

International Search Report and Written Opinion received for PCT Patent Application No. PCT/US17/28466, mailed on Jul. 5, 2017, 8 pages.

International Search Report and Written Opinion received for PCT Patent Application No. PCT/US19/58676, mailed on Jan. 16, 2020, 6 pages.

International Search Report and Written Opinion received for PCT Patent Application No. PCT/US2023/020407, mailed on Jul. 26, 2023, 10 pages.

International Search Report and Written Opinion received for PCT Patent Application No. PCT/US2023/020417, mailed on Jul. 21, 2023, 11 pages.

International Search Report and Written Opinion received for PCT Patent Application No. PCT/US17/28465, mailed on Jul. 5, 2017, 7 pages.

International Search Report and Written Opinion received for PCT Patent Application No. PCT/US20/017555, mailed on May 4, 2020, 8 pages.

International Search Report and Written Opinion received for PCT Patent Application No. PCT/US20/37289, mailed on Sep. 30, 2020, 8 pages.

(56) References Cited

OTHER PUBLICATIONS

International Search Report and Written Opinion received for PCT Patent Application No. PCT/US2014/031237, mailed on Jul. 15, 2014, 11 pages.
International Search Report and Written Opinion received for PCT Patent Application No. PCT/US2017/021886, mailed on Jun. 1, 2017, 15 pages.
International Search Report and Written Opinion received for PCT Patent Application No. PCT/US2018/062093, mailed on Feb. 1, 2019, 7 pages.
International Search Report and Written Opinion received for PCT Patent Application No. PCT/US2018/062096, mailed on Feb. 11, 2019, 13 pages.
International Search Report and Written Opinion received for PCT Patent Application No. PCT/US2019/027214, mailed on Jun. 25, 2019, 14 pages.
International Search Report and Written Opinion received for PCT Patent Application No. PCT/US2019/048357, mailed on Nov. 18, 2019, 13 pages.
International Search Report and Written Opinion received for PCT Patent Application No. PCT/US2020/016952, mailed on Apr. 22, 2020, 9 pages.
International Search Report and Written Opinion received for PCT Patent Application No. PCT/US2020/017552, mailed on May 4, 2020, 9 pages.
International Search Report and Written Opinion received for PCT Patent Application No. PCT/US2020/017556, mailed on May 4, 2020, 12 pages.
International Search Report and Written Opinion received for PCT Patent Application No. PCT/US2020/033159, mailed on Aug. 12, 2020, 9 pages.
International Search Report and Written Opinion received for PCT Patent Application No. PCT/US2021/063559, mailed on Mar. 18, 2022, 9 pages.
International Search Report and Written Opinion received for PCT Patent Application No. PCT/US21/045186, mailed on Nov. 22, 2021, 10 pages.
International Search Report and Written Opinion received for PCT Patent Application No. PCT/US21/17078, mailed on Apr. 23, 2021, 9 pages.
International Search Report and Written Opinion received for PCT Patent Application No. PCT/US22/36030, mailed on Oct. 7, 2022, 7 pages.
International Search Report and Written Opinion received for PCT Patent Application No. PCT/US22/49036, mailed on Mar. 8, 2023, 9 pages.
International Search Report and Written Opinion received for PCT Patent Application No. PCT/US24/17857, mailed on May 10, 2024, 10 pages.
Invitation to Respond to Written Opinion issued by the Intellectual Property Office of Singapore dated Dec. 28, 2016 for corresponding Singapore Patent Application No. 11201506780R.
It Really is in Your Blood: Glucose to Ketone Ratios. Greymadder, Sep. 15, 2014. Downloaded Apr. 1, 2015. http://greymadder.net/2014/09/15/it-really-is-in-your-blood-glucose-to-ketone-ratios/.
James, "Optical Purity and Enantiomeric Excess" at https://www.masterorganicchemistry.com/2017/02/24/optical-purity-and-enantiomeric-excess/. (Retrieved from the internet Nov. 6, 2018) (Year: 2018).
John C Newman et al: "beta-Hydroxybutyrate: A Signaling Metabolite", Annual Review of Nutrition, vol. 37, Aug. 21, 2017 (Aug. 21, 2017), pp. 51-76, XP055771586.
Kackley et al., "A Pre-Workout Supplement of Ketone Salts, Caffeine, and Amino Acids Improves High-Intensity Exercise Performance in Keto-Naïve and Keto-Adapted Individuals", Journal of the American College of Nutrition, Apr. 24, 2020, vol. 39, No. 4, pp. 290-300.
Karppanen, H., et al, "Why and how to implement sodium, potassium, calcium, and magnesium changes in food items and diets?" J. Human Hypertension (2005), vol. 19, pp. S10-S19.
Kaster M.P. et al, "Caffeine acts through neuronal adenosine A2A receptors to prevent mood and memory dysfunction triggered by chronic stress", Proceedings of the National Academy of Sciences, vol. 112, No. 25, Jun. 8, 2015, pp. 7833-7838.
Kesl, et al., "Effects of exogenous ketone supplementation on blood ketone, glucose, triglyceride, and lipoprotein levels in Sprague-Dawley rats", Nutrition & Metabolism (2016).
Desrochers et al., "Metabolism of R- and S-1,3-butanediol in perfused livers from meal-fed and starved rats", Biochem. J., 1992, vol. 285, pp. 647-653.

* cited by examiner

Figure 1

| Subject | Condition | Baseline | 30 minutes | 60 minutes | 90 minutes | 120 minutes | 180 minutes |
|---|---|---|---|---|---|---|---|
| A | 10g DL-BHB | 0.2 | 0.7 | 0.5 | 0.3 | 0.2 | 0.2 |
| B | 10g DL-BHB | 0.1 | 0.9 | 0.6 | 0.3 | 0.2 | 0.2 |
| C | 10g DL-BHB | 0.1 | 0.5 | 0.2 | 0.1 | 0.1 | 0.1 |
| D | 10g DL-BHB | 0.2 | 0.8 | 0.6 | 0.3 | 0.2 | 0.1 |
| Average | | 0.15 | 0.725 | 0.475 | 0.25 | 0.175 | 0.15 |
| A | 10g R-BHB | 0.2 | 1.8 | 0.7 | 0.4 | 0.3 | 0.2 |
| B | 10g R-BHB | 0.2 | 1.5 | 0.7 | 0.3 | 0.2 | 0.2 |
| C | 10g R-BHB | 0.1 | 0.7 | 0.3 | 0.2 | 0.2 | 0.1 |
| D | 10g R-BHB | 0.1 | 1.5 | 1.2 | 0.6 | 0.2 | 0.2 |
| Average | | 0.15 | 1.375 | 0.725 | 0.375 | 0.225 | 0.175 |
| A | 5g R-BHB | 0.3 | 0.6 | 0.3 | 0.4 | 0.3 | 0.4 |
| B | 5g R-BHB | 0.1 | 0.8 | 0.7 | 0.2 | 0.2 | 0.2 |
| C | 5g R-BHB | 0.1 | 0.4 | 0.2 | 0.2 | 0.2 | 0.1 |
| D | 5g R-BHB | 0.1 | 0.7 | 0.3 | 0.2 | 0.1 | 0.1 |
| Average | | 0.15 | 0.625 | 0.375 | 0.25 | 0.2 | 0.2 |

Total Fat Mass Results

| Scan Date | Age | Fat Mass (g) | Change/Month vs | | Change vs | |
|---|---|---|---|---|---|---|
| | | | Baseline | Previous | Baseline | Previous |
| 12/17/2016 | 51 | 32748 | -1545 | -1545 | -5177 | -5177 |
| 09/05/2016 | 51 | 37925 | | | | |

DL BHB vs. R BHB on 2km Time Trial Improvement

Delta Change in Perceived Exertion at High Intensity Cycling Exercise Using DL BHB vs. R BHB Figure 14A
Figure 14B
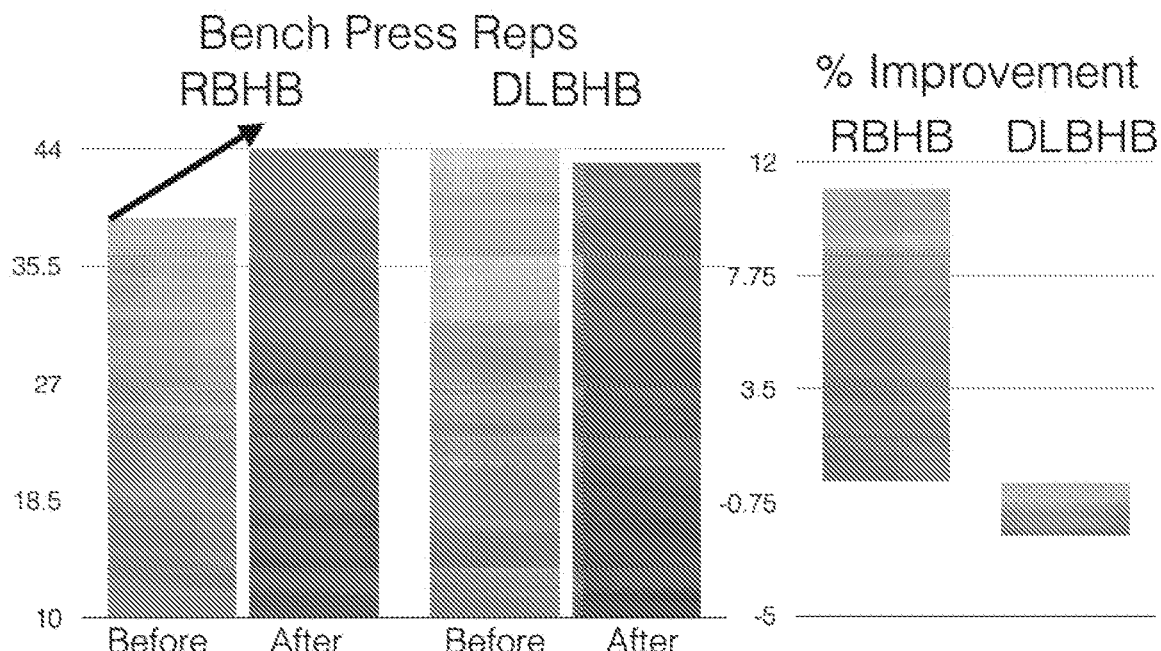
Figure 14C
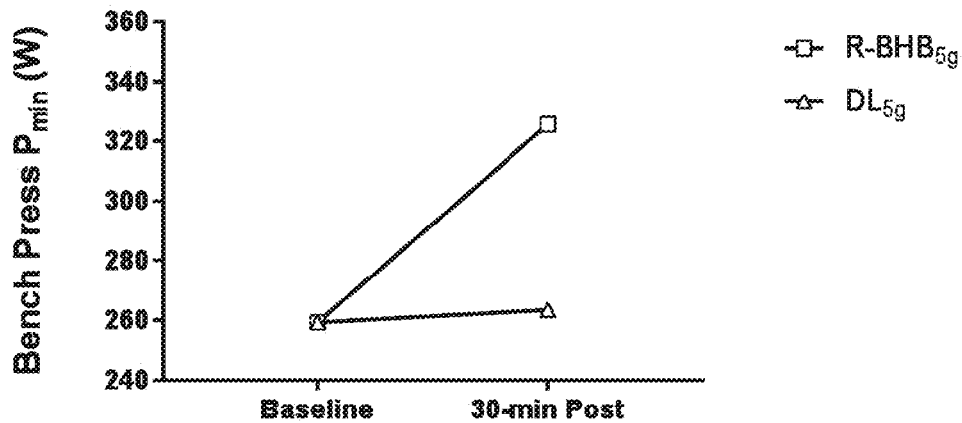

COMPOSITIONS AND COMPOUNDS CONTAINING KETONE BODIES AND/OR KETONE BODY PRECURSORS AND ONE OR MORE AMINO ACIDS

CROSS-REFERENCE TO RELATED APPLICATIONS

This application is a continuation-in-part of U.S. patent application Ser. No. 18/977,541, filed Dec. 11, 2024, which is a continuation of U.S. patent application Ser. No. 18/219, 556, filed Jul. 7, 2023, now U.S. Pat. No. 12,251,362, which is a continuation of U.S. patent application Ser. No. 17/367, 206, filed Jul. 2, 2021, now U.S. Pat. No. 12,109,182, which is a continuation-in-part of U.S. patent application Ser. No. 15/491,924, filed Apr. 19, 2017, now U.S. Pat. No. 11,173, 138, which claims the benefit of U.S. Provisional Application No. 62/324,798, filed Apr. 19, 2016, the foregoing of which are incorporated herein by reference in their entirety.

TECHNICAL FIELD

The present invention relates to administration of butyrate, beta-hydroxybutyrate, other ketone bodies or ketone body precursors, amino acids, and related compounds and compositions.

BACKGROUND

Currently, beta-hydroxybutyrate salts can be administered orally or intravenously in humans to promote weight loss and/or ketosis. However, the excess intake of salts such as sodium, magnesium, and potassium may be unwarranted (e.g., high blood pressure, stroke, damage to organs, gastrointestinal problems, etc.). Thus, many people may not be able to tolerate administration of beta-hydroxybutyrate salts in amounts to promote or sustain weight loss and/or ketosis. Polymers of beta-hydroxybutyrate have also been administered to humans to promote ketosis. However, since polymers must be processed by the body to deliver beta-hydroxybutyrate to the individual, the delivery is slow and/or a larger amount of the polymer must be administered to deliver a specified amount of beta-hydroxybutyrate.

SUMMARY

Disclosed are compounds in which at least one ketone body or ketone body precursor (collectively "ketone body component"), such as beta-hydroxybutyrate, acetoacetate, 1,3-butanediol, or medium chain fatty acid, is complexed with or coupled to an amino acid in order to provide a composition that provides specific benefits to the body, including benefits that target certain regions and/or biochemical processes in the body. The beta-hydroxybutyrate and acetoacetate can be provided in acid, salt, and/or ester forms. The 1,3-butanediol or medium chain fatty acid can be provided in monomeric and/or ester forms.

In some embodiments, the composition may include a complex between at least a portion of the ketone body component and at least a portion of the amino acid component. In addition or alternatively, the composition may include a covalent bond between at least a portion of the ketone body component and at least a portion of the amino acid component, such as an ester bond formed between the hydroxyl group of beta-hydroxybutyrate and/or 1,3-butanediol and the carboxyl group of an amino acid, or it may include an amide bond formed between the carboxyl group of beta-hydroxybutyrate, acetoacetate, and/or medium chain fatty acid and the amine of an amino acid.

In some embodiments, a ketone body, i.e., beta-hydroxybutyrate, such as R-beta-hydroxybutyrate or acetoacetate, or a ketone body precursor, such as 1,3-butanediol or medium chain fatty acid, can be complexed with and/or bonded to an amino acid selected from the group consisting of leucine, lysine, arginine, histidine, ornithine, creatine, agmatine, citrulline, isoleucine, valine, glutamine, tryptophan, tyrosine, phenylalanine, glycine, beta-alanine, proline, methionine, threonine, and taurine. The association between the ketone body component and the amino acid component can be a complex, as understood by those skilled in the art, or it can be chemical bond as discussed above.

Complexing or coupling a ketone body such as beta-hydroxybutyrate or acetoacetate, or a ketone body precursor such as 1,3-butanediol or medium chain fatty acid (collectively "ketone body component"), to an amino acid provides health benefits, enhanced bioavailability, and muscle repair. The ketone body-amino acid composition provides unexpected results compared to beta-hydroxybutyrate and acetoacetate salts or free 1,3-butanediol or medium chain fatty acid, such as being engineered to travel further into the digestive system to act as treatment for gut related issues or feed the microbiome or be a time release formula.

Other benefits include increased energy and enhanced ketosis, enhanced cognitive and neurological function, increased muscle and physical performance, enhanced metabolic and cellular repair, improved detoxification and gut health, targeted bioavailability, sustained release and controlled absorption, increased metabolic efficiency, enhanced cellular uptake, minimized side effects, and multifunctional therapeutics.

In various implementations, a pharmaceutically effective amount of butyrate, ketone body (i.e., beta-hydroxybutyrate or acetoacetate), ketone body precursor (e.g., 1,3-butanediol or medium chain fatty acid), amino acid, related compounds, and/or one or more other compounds may be administered to an individual. For example, the pharmaceutically effective amount of the beta-hydroxybutyrate or other ketone body or ketone body precursor, amino acid, related compounds, and/or one or more other compounds may be administered to cause weight loss, assist weight maintenance, elevate blood ketone levels, maintain blood ketone levels, reduce blood glucose levels, maintain blood glucose levels, improve focus, improve energy, improve cognitive function, treat traumatic brain injury, treat diabetes, treat neurological disorders, treat cancer, treat inflammatory conditions, suppress appetite, provide anti-aging effects, anti-glycation, treat epilepsy, treat depression, improve performance, improve strength, improve muscle mass, promote fat loss, improve body composition, and/or for use as a medicament, etc. The pharmaceutically effective amount of butyrate, beta-hydroxybutyrate or other ketone body or ketone body precursor, amino acid, related compounds, and/or combinations thereof may be administered to healthy individuals and/or not healthy individuals (e.g., with diseases and/or disorders).

Implementations may include one or more of the following features. The beta-hydroxybutyrate or 1,3-butanediol may include the racemic mixture and/or the individual isomers of beta-hydroxybutyrate, such as R-beta-hydroxybutyrate (also known as D-beta-hydroxybutyrate), or 1,3-butanediol, such as R-1,3-butanediol, either optically pure or enriched in the R-enantiomer compared to the S-enantiomer. The beta-hydroxybutyrate, acetoacetate, or ketone body precursor may include related compounds. The ketone body (e.g., beta-hydroxybutyrate or acetoacetate) or ketone body precursor may be complexed with and/or coupled (i.e., covalently bonded) to a compound such as an amino acid to provide specific benefits to the body. The beta-hydroxybutyrate or acetoacetate may include one or more beta-hydroxybutyrate or acetoacetate salts, one or more beta-hydroxybutyrate or acetoacetate esters, or their free acid forms. Other compounds may include short chain fatty acids, short chain triglycerides, medium chain fatty acids, medium chain triglycerides, long chain fatty acids, long chain triglycerides, berberine, berberine metabolites, dihydroberberine, tetrahydroberberine and/or combinations thereof. One or more of the other compounds may be unencapsulated and/or encapsulated.

In various implementations, a composition may be administered to induce and/or maintain ketosis. The composition may include approximately 0.5 g to approximately 10 g of R-beta-hydroxybutyrate, acetoacetate, or ketone body precursor.

Implementations may include one or more of the following features. The amount of the composition administered may include approximately 0.5 to approximately 3 g of R-beta-hydroxybutyrate, acetoacetate, or ketone body precursor. The composition may include additional components, such as components and compositions that are capable of independently increasing ketone levels, inducing ketosis, and/or maintaining ketosis. In some implementations, the composition may include additional component and compositions to provide other health benefits (e.g., increase mental acuity, strength, etc.). For example, the composition may include fatty acids and/or esters of fatty acids. For example, the composition may include a short chain fatty acid, an ester of short chain fatty acid, a medium chain fatty acid, an ester of medium chain fatty acid, a long chain fatty acid, or an ester of long chain fatty acid. The composition may include flavoring(s), vitamin(s), mineral(s), and/or binder(s).

The composition may be administered up to 5 times daily. The administration of the composition may increase strength, mental acuity, metabolism, fat loss, fat oxidation, motor function, muscle mass, and/or combinations thereof. In some implementations, the 0.5 to 10 g of R-beta-hydroxybutyrate administered includes R-beta-hydroxybutyrate and at least one of a polymer of R-beta-hydroxybutyrate or R-beta-hydroxybutyrate-complex.

In various implementations, a composition may include approximately 0.5 g to approximately 10 g of R-beta-hydroxybutyrate and one or more additional compounds capable of maintaining ketosis independently (e.g., acetoacetate or ketone body precursor, such as 1,3-butanediol or medium chain fatty acid). Administration of the composition may induce and/or maintains ketosis in an individual.

Implementations may include one or more of the following features. The R-beta-hydroxybutyrate may include R-beta-hydroxybutyrate salt, R-beta-hydroxybutyrate-amino acid complex, R-beta-hydroxybutyrate-amino acid compound, and/or R-beta-hydroxybutyrate polymer. The acetoacetate may include acetoacetate salt, acetoacetate-amino acid complex, or acetoacetate-amino acid compound, and/or acetoacetate ester. The additional compounds may include fatty acids and/or esters of fatty acids. The fatty acids and/or esters may include natural (e.g., cream, coconut oil, macadamia oil, etc.) and/or artificial fatty acids and/or esters of fatty acids. For example, the composition may include a short chain fatty acid, an ester of short chain fatty acid, a medium chain fatty acid, an ester of medium chain fatty acid, a long chain fatty acid, or an ester of long chain fatty acid. In some implementations, additional compound(s) may include polymer(s) of beta-hydroxybutyrate, D,L-beta-hydroxybutyrate, butyrate, butyric acid, and/or triglyceride tributyrin. The additional compound(s) may include berberine, dihydroberberine, and/or tetrahydroberberine.

In various implementations, pharmaceutically effective amounts of R-beta-hydroxybutyrate, acetoacetate, or ketone body precursor and amino acid may be administered for inducing and/or maintaining ketosis.

Implementations may include one or more of the following features. The amount of R-beta-hydroxybutyrate, acetoacetate, or ketone body precursor to induce and/or maintain ketosis in an individual may be less than or equal to half of the amount of D,L-beta-hydroxybutyrate to induce and/or maintain the same level of ketosis (e.g., as measured by blood ketone levels). In some implementations, the amount of R-beta-hydroxybutyrate, acetoacetate, or ketone body precursor to induce and/or maintain ketosis in an individual may be less than the amount of D,L-beta-hydroxybutyrate or L-beta-hydroxybutyrate to induce and/or maintain the same level of ketosis. The composition may include approximately 1 g to approximately 5 grams of R-beta-hydroxybutyrate, acetoacetate, or ketone body precursor and approximately 0.5 to 2 g of amino acid. The amino acid may include leucine. The composition may include a mixture and/or complex of the R-beta-hydroxybutyrate, acetoacetate, or ketone body precursor and amino acid. At least a portion of the R-beta-hydroxybutyrate, acetoacetate, or ketone body precursor may be complexed with or coupled to the amino acid, in some implementations. For example, a portion of the R-beta-hydroxybutyrate may be administered in the composition as a salt and/or polymer and another portion of the R-beta-hydroxybutyrate may be administered as a complex with or coupled to an amino acid (e.g., leucine). In some implementations, the composition may include at least one R-beta-hydroxybutyrate salt (e.g., in additional to the pharmaceutically effective amounts of R-beta-hydroxybutyrate in the composition and/or as the pharmaceutically effective amounts of R-beta-hydroxybutyrate).

In various implementations, a composition for maintaining or increasing weight loss may include approximately 0.5 g to approximately 15 g of R-beta-hydroxybutyrate, acetoacetate, or ketone body precursor, one or more flavorings, one or more vitamins, one or more minerals, one or more binders, and/or one or more liquid carriers. The R-beta-hydroxybutyrate or acetoacetate can be in their free acid form, one or more salts, or one or more esters. The composition may be orally administered to maintaining and/or increasing weight loss in an individual.

Implementations may include one or more of the following features. The liquid carrier may include water. The amount of R-beta-hydroxybutyrate or acetoacetate salt may include approximately 0.5 to approximately 5 g of R-beta-hydroxybutyrate or acetoacetate salt. The composition may include at least one polymer of beta-hydroxybutyrate and at least one salt of R-beta-hydroxybutyrate. The administration of the composition increases mental acuity. The administration of the composition increases at least one of metabolism, fat loss, fat oxidation, motor function, and/or muscle mass. The composition may be administered up to 5 times daily. The R-beta-hydroxybutyrate or acetoacetate salt in the composition may include sodium R-beta-hydroxybutyrate or acetoacetate, potassium R-beta-hydroxybutyrate or acetoacetate, magnesium R-beta-hydroxybutyrate or acetoacetate, and/or calcium R-beta-hydroxybutyrate or acetoacetate.

In various implementations, a composition for maintaining or inducing ketosis may include approximately 0.5 g to approximately 15 g of R-beta-hydroxybutyrate, acetoacetate, or ketone body precursor, one or more flavorings, one or more vitamins, one or more minerals, one or more binders, and/or one or more liquid carriers. The R-beta-hydroxybutyrate comprises one or more salts of R-beta-hydroxybutyrate salt. The composition may be orally administered to maintain and/or induce ketosis in an individual.

Implementations may include one or more of the following features. The amount of R-beta-hydroxybutyrate salt in the composition may include approximately 0.5 to approximately 5 g of R-beta-hydroxybutyrate salt. The one or more salts of R-beta-hydroxybutyrate may include sodium R-beta-hydroxybutyrate, potassium R-beta-hydroxybutyrate, calcium R-beta-hydroxybutyrate, and/or magnesium R-beta-hydroxybutyrate. The liquid carrier may include water, milk, and/or coconut water. The administration of the composition may increase metabolism, fat loss, fat oxidation, motor function, and/or muscle mass. The administration of the compound may increase mental acuity, cognitive functioning, mood, energy, alertness, focus, and/or performance.

In various implementations, a composition for maintaining or inducing ketosis may include approximately 0.5 g to approximately 15 g of R-beta-hydroxybutyrate or acetoacetate, an additional compound (i.e., ketone body precursor) capable of increasing ketone levels independently, one or more flavorings, one or more vitamins, one or more minerals, one or more binders, and/or one or more liquid carriers. The R-beta-hydroxybutyrate comprises one or more salts of R-beta-hydroxybutyrate salt. The additional compound may include less than approximately 500 mg of caffeine. The composition may be orally administered to maintain and/or induce ketosis in an individual.

Implementations may include one or more of the following features. The composition may include approximately 5 mg to approximately 50 mg of caffeine. The composition comprises include approximately 0.5 g to approximately 5 g of R-beta-hydroxybutyrate, acetoacetate, or ketone body precursor and approximately 5 mg to approximately 50 mg of caffeine. The one or more salts of R-beta-hydroxybutyrate may include sodium R-beta-hydroxybutyrate, potassium R-beta-hydroxybutyrate, calcium R-beta-hydroxybutyrate, and/or magnesium R-beta-hydroxybutyrate. The administration of the composition may increase at least one of weight loss, metabolism, fat loss, fat oxidation, motor function, muscle mass, mental acuity, cognitive functioning, mood, energy, alertness, focus, and/or performance. The liquid carrier may include water, milk, and/or coconut water.

The details of one or more implementations are set forth in the accompanying drawings and the description below. Other features, objects, and advantages of the implementations will be apparent from the description and drawings.

BRIEF DESCRIPTION OF THE DRAWINGS

For a more complete understanding of this disclosure and its features, reference is now made to the following description, taken in conjunction with the accompanying drawings, in which:

FIG. 1 illustrates a table of blood ketone levels over time for 4 subjects for an implementation of an example administration of D,L-beta-hydroxybutyrate and R/D-beta-hydroxybutyrate.

FIG. 14A illustrates a chart illustrating strength test results following an implementation of an example administration protocol.

FIG. 14B illustrates a chart illustrating strength test results following an implementation of an example administration protocol.

FIG. 14C illustrates a chart illustrating power test results following an implementation of an example administration protocol.

Like reference symbols in the various drawings indicate like elements.

DETAILED DESCRIPTION

Figure 2:
FIG. 2 illustrates a table of blood ketone levels over time for an implementation of an example administration of the microencapsulated butyrate compared to traditional sodium butyrate.

In various implementations, compounds such as butyrate, beta-hydroxybutyrate, acetoacetate, ketone body precursor, and/or related compounds (e.g., derivatives, esters, polymers, etc.) can be administered alone or in combination with one or more other compounds. Administration of a pharmaceutically effective amount of these compound(s) may promote and/or maintain weight loss and/or ketosis. In some implementations, blood ketone levels and/or blood glucose levels may be reduced and/or maintained within a predetermined range when a pharmaceutically effective amount of one or more compounds are administered. In some implementations, a health of an individual (e.g., strength, symptoms of disease, mental acuity, fasting glucose levels, etc.) may be improved and/or maintained by administration of a compound that includes butyrate, beta-hydroxybutyrate and/or related compounds (e.g., derivatives, esters, polymers, etc.).

In various implementations butyrate, beta-hydroxybutyrate, acetoacetate, ketone body precursor, amino acid, and/or related compounds may be administered to a human. Beta-hydroxybutyrate (e.g., R-beta-hydroxybutyrate, L-beta-hydroxybutyrate, and/or D,L-beta-hydroxybutyrate) may include ketone body acids, salts, and/or esters. In some embodiments, compositions may include beta-hydroxybutyrate, acetoacetate, or ketone body precursor bound (e.g., complexed or coupled) to another compound (e.g., amino acids) and/or polymers of beta-hydroxybutyrate.

For example, beta-hydroxybutyrate (e.g., R-beta-hydroxybutyrate, L-beta-hydroxybutyrate, and/or D,L-beta-hydroxybutyrate) or acetoacetate may include beta-hydroxybutyrate or acetoacetate salts, beta-hydroxybutyrate or acetoacetate esters, beta-hydroxybutyrate or acetoacetate sodium salt (e.g., sodium beta-hydroxybutyrate or acetoacetate), beta-hydroxybutyrate or acetoacetate potassium salt (e.g., potassium beta-hydroxybutyrate or acetoacetate), beta-hydroxybutyrate or acetoacetate calcium salt (e.g., calcium beta-hydroxybutyrate or acetoacetate), beta-hydroxybutyrate or acetoacetate magnesium salt (e.g., magnesium beta-hydroxybutyrate or acetoacetate), beta-hydroxybutyrate or acetoacetate lithium salt (e.g., lithium beta-hydroxybutyrate or acetoacetate).

The compositions may include complexes (e.g., salts) or compounds (e.g., esters or amides) between a ketone body and amino acid, such as arginine beta-hydroxybutyrate or acetoacetate, lysine beta-hydroxybutyrate or acetoacetate, histidine beta-hydroxybutyrate or acetoacetate, ornithine beta-hydroxybutyrate or acetoacetate, creatine beta-hydroxybutyrate or acetoacetate, agmatine beta-hydroxybutyrate or acetoacetate, or citrulline beta-hydroxybutyrate or acetoacetate, other appropriate organic salts that include beta-hydroxybutyrate or acetoacetate, and/or combinations thereof. Other examples include complexes and compounds between a ketone body or ketone body precursor and an amino acid, such as leucine, lysine, arginine, histidine, ornithine, creatine, agmatine, citrulline, isoleucine, valine, glutamine, tryptophan, tyrosine, phenylalanine, glycine, beta-alanine, proline, methionine, threonine, and taurine.

In some implementations, beta-hydroxybutyrate or acetoacetate may include beta-hydroxybutyrate or acetoacetate salts including (calcium, sodium, magnesium, potassium, zinc, selenium, chromium, other appropriate minerals, and/or combinations thereof. In some implementations, the beta-hydroxybutyrate, acetoacetate, or ketone body precursor may be complexed and/or coupled to another compound (e.g., amino acid and/or berberine) and a beta-hydroxybutyrate or acetoacetate salt may include a complex (e.g., chelate) that includes a mineral (e.g., calcium, zinc, etc.) and the beta-hydroxybutyrate or acetoacetate compound coupled to another compound. The beta-hydroxybutyrate may include single isomer beta-hydroxybutyrate and/or polymer beta-hydroxybutyrate. For example, R-beta-hydroxybutyrate may include single isomer R-beta-hydroxybutyrate and/or polymer R-beta-hydroxybutyrate. In some implementations, beta-hydroxybutyrate may be administered with 1,3-butanediol, ethyl acetoacetate, ethyl beta-hydroxybutyrate, or medium chain fatty acid.

The beta-hydroxybutyrate or 1,3-butanediol may include racemic mixtures and/or individual isomers of beta-hydroxybutyrate or 1,3-butanediol. In some implementations, one or more specific chiralities of beta-hydroxybutyrate or 1,3-butanediol may be utilized. For example, R-beta-hydroxybutyrate (also referred to as D-beta-hydroxybutyrate), S-beta-hydroxybutyrate (also referred to as L-beta-hydroxybutyrate), R-1,3-butanediol, S-1,3-butanediol, and/or mixtures (e.g., racemic mixtures) thereof may be utilized. In some implementations, R-beta-hydroxybutyrate may be included in the composition (e.g., a more purified form of R-beta-hydroxybutyrate rather than D,L-beta-hydroxybutyrate). For example, R-beta-hydroxybutyrate may include less than approximately 10%, less than approximately 5%, or less than approximately 1% L-beta-hydroxybutyrate (corresponding to greater than approximately 90%, greater than approximately 95%, or greater than approximately 99% R-beta-hydroxybutyrate). R-beta-hydroxybutyrate may have a greater bioavailability than other chiralities of beta-hydroxybutyrate. R-beta-hydroxybutyrate may have a greater impact on a health of an individual (e.g., due to decreased side effects; increase ketone levels, weight loss, mental acuity, fat loss, etc.) than L-beta-hydroxybutyrate and/or D,L-beta-hydroxybutyrate. In some implementations, R-beta-hydroxybutyrate may cause improvements in health not capable by L-beta-hydroxybutyrate and/or D,L-beta-hydroxybutyrate. R-beta-hydroxybutyrate may have less impurities due to manufacturing, such as less crotonic acid (e.g., which can be harmful to individuals), than other forms of beta-hydroxybutyrate (e.g., L-beta-hydroxybutyrate and/or D,L-beta-hydroxybutyrate). In some implementations, R-beta-hydroxybutyrate may be more capable of binding (i.e., covalently bonding) with other compounds (e.g., purine, lysine, potassium, and/or other amino acids; dihydroberberine; etc.) to deliver the beta-hydroxybutyrate to a human. Thus, R-beta-hydroxybutyrate (e.g., greater than 90% purity of R-beta-hydroxybutyrate and less than 10% L-beta-hydroxybutyrate) and/or mixtures with R-beta-hydroxybutyrate may be administered to humans. In some implementations, unexpectedly, a smaller amount of R-beta-hydroxybutyrate may be as pharmaceutically effective (e.g., in increasing and/or maintaining weight loss; in increasing and/or maintaining elevated ketone levels, etc.) or more pharmaceutically effective as D,L-beta-hydroxybutyrate (e.g., racemic mixture of D- and L-beta-hydroxybutyrate). For example, approximately half an amount of R-beta-hydroxybutyrate may be administered to achieve the approximately the same efficacy as D,L-beta-hydroxybutyrate and/or L-beta-hydroxybutyrate. The R-beta-hydroxybutyrate may be more bioavailable than other chiralities of beta-hydroxy butyrate and thus allow a smaller effective amount than other chiralities. Thus, by utilizing R-beta-hydroxybutyrate, the administration amount of beta-hydroxybutyrate to be reduced (e.g., when compared to the administration amount of D,L-beta-hydroxybutyrate) while providing a pharmaceutically effective amount, such as (e.g., for weight loss and/or maintenance; for elevating and/or maintaining blood ketone levels). Reducing the amount of beta-hydroxybutyrate, when the beta-hydroxy butyrate is provided in salt form, may reduce a user's intake of the cation of the salt (e.g., sodium, potassium, etc.). Since intake of some of these cations in beta-hydroxybutyrate salts, such as sodium, potassium, magnesium, and calcium, in amounts greater than a predetermined recommended amount may cause health problems (e.g., organ damage, gastrointestinal problems, etc.), reducing the amount of beta-hydroxybutyrate salt by using R-beta-hydroxybutyrate may inhibit side effects and/or health problems associated salts combined with beta-hydroxybutyrate administration in users.

In some implementations, a pharmaceutically effective amount of R-beta-hydroxybutyrate, acetoacetate, or ketone body precursor may be administered in an individual to promote and/or maintain ketosis, cause weight loss and/or manage weight, and/or increase blood ketone levels. For example, approximately 0.1 g to approximately 50 g of R-beta-hydroxybutyrate, acetoacetate, or ketone body precursor may be administered to an individual. In some implementations, approximately 0.1 g to approximately 15 g of R-beta-hydroxybutyrate, acetoacetate, or ketone body precursor may be administered to an individual. In some implementations, approximately 1 g to approximately 10 g of beta-hydroxybutyrate, acetoacetate, or ketone body precursor may be administered, for example, once a day to 5 times a day (e.g., to administer up to 50 g of beta-hydroxybutyrate, acetoacetate, or ketone body precursor). The administration may cause weight loss and/or maintenance; elevated beta-hydroxybutyrate and acetoacetate levels in the blood; elevated, reduced, and/or maintenance of blood ketone levels; induction and/or maintenance of ketosis; and/or reduction; improve mental acuity; improve focus; improve energy; improve cognitive function; reduce traumatic brain injury; improve diabetes; improve glucose tolerance; decrease blood glucose levels; reduce neurological disorders and/or symptoms thereof; improve cancer and/or symptoms thereof; improve inflammatory conditions; suppressing appetite; improve symptoms associated with aging; provide anti-glycation affects; improve epilepsy and/or symptoms thereof; improve depression and/or symptoms thereof; improve performance; improve strength; increase muscle mass; increase fat loss; improve body composition; improve energy; improve focus; improve cognitive function; improve mood and/or well-being; and/or combinations thereof. The beta-hydroxybutyrate (e.g., R-beta-hydroxybutyrate) may be administered in healthy and not healthy individuals (e.g., individuals with diseases and/or disorders).

In some implementations, the beta-hydroxybutyrate, such as R-beta-hydroxybutyrate, acetoacetate, or ketone body precursor, may be administered with, complexed with, and/or coupled (i.e., covalently bonded) to a compound such as an amino acid. For example, beta-hydroxybutyrate, acetoacetate, or ketone body precursor may be coupled to amino acids, such as leucine, lysine, arginine, histidine, ornithine, creatine, agmatine, citrulline and/or combinations thereof. Other amino acids that can be complexed with or coupled to beta-hydroxybutyrate, acetoacetate, or ketone body precursor include isoleucine, valine, glutamine, tryptophan, tyrosine, phenylalanine, glycine, beta-alanine, proline, methionine, threonine, and taurine. The chemical bond can be an ester linkage, such as between the hydroxyl group of beta-hydroxybutyrate or 1,3-butanediol and a carboxyl group of the amino acid. Alternatively, the chemical bond can be an ester linkage between the carboxyl group of beta-hydroxybutyrate and the hydroxyl group of an amino acid that has a hydroxyl group. In yet other embodiments, the chemical bond can be an amide linkage, such as between the carboxyl group of beta-hydroxybutyrate acetoacetate, or medium chain fatty acid and the amine group of the amino acid.

As will be shown in more detail in the Examples below, the beta-hydroxybutyrate, acetoacetate, or ketone body precursor and amino acid complexes and compounds disclosed herein can provide specific benefits and synergies. For example, the following beta-hydroxybutyrate, acetoacetate, or ketone body precursor and amino acid complexes and compounds provide energy and ketosis enhancement: beta-hydroxybutyrate, acetoacetate, or ketone body precursor complexed with or covalently bonded to isoleucine; beta-hydroxybutyrate, acetoacetate, or ketone body precursor complexed with or covalently bonded to valine; and beta-hydroxybutyrate, acetoacetate, or ketone body precursor complexed with or covalently bonded to glutamine.

The following beta-hydroxybutyrate, acetoacetate, or ketone body precursor and amino acid compounds enhance cognitive and neurological function: beta-hydroxybutyrate, acetoacetate, or ketone body precursor complexed with or covalently bonded to tryptophan; beta-hydroxybutyrate, acetoacetate, or ketone body precursor complexed with or covalently bonded to tyrosine; beta-hydroxybutyrate, acetoacetate, or ketone body precursor complexed with or covalently bonded to phenylalanine; and beta-hydroxybutyrate, acetoacetate, or ketone body precursor complexed with or covalently bonded to glycine.

The following beta-hydroxybutyrate, acetoacetate, or ketone body precursor and amino acid compounds enhance muscle and physical performance: beta-hydroxybutyrate, acetoacetate, or ketone body precursor complexed with or covalently bonded to leucine; beta-hydroxybutyrate, acetoacetate, or ketone body precursor complexed with or covalently bonded to arginine; beta-hydroxybutyrate complexed with or covalently bonded to citrulline; and beta-hydroxybutyrate, acetoacetate, or ketone body precursor complexed with or covalently bonded to beta-alanine.

The following beta-hydroxybutyrate, acetoacetate, or ketone body precursor and amino acid compounds enhance metabolic and cellular repair: beta-hydroxybutyrate, acetoacetate, or ketone body precursor complexed with or covalently bonded to lysine; beta-hydroxybutyrate, acetoacetate, or ketone body precursor complexed with or covalently bonded to proline; beta-hydroxybutyrate, acetoacetate, or ketone body precursor complexed with or covalently bonded to methionine; and beta-hydroxybutyrate, acetoacetate, or ketone body precursor complexed with or covalently bonded to threonine.

The following beta-hydroxybutyrate, acetoacetate, or ketone body precursor and amino acid compounds enhance detoxification and gut health: beta-hydroxybutyrate, acetoacetate, or ketone body precursor complexed with or covalently bonded to taurine; and beta-hydroxybutyrate, acetoacetate, or ketone body precursor complexed with or covalently bonded to ornithine.

Compounds made by coupling (i.e., covalently bonding) beta-hydroxybutyrate, acetoacetate, or ketone body precursor to an amino acid provide the following additional general benefits:

1. Targeted Bioavailability:
  covalent bonding allows precise delivery of beta-hydroxybutyrate and amino acids to target tissues (e.g., muscle, brain);

specificity can enhance therapeutic outcomes, such as muscle recovery or cognitive function.

2. Sustained Release and Controlled Absorption:
   covalent bonds can be engineered for slow hydrolysis, leading to sustained ketone release;
   maintains stable blood ketone levels over time, reducing the frequency of administration.

3. Increased Metabolic Efficiency:
   covalent beta-hydroxybutyrate-amino acid complexes may enter metabolic pathways more efficiently, reducing energy loss during conversion;
   supports ATP production directly and minimizes metabolic waste.

4. Enhanced Cellular Uptake:
   covalent complexes are more likely to be recognized and transported by amino acid-specific carriers, bypassing competitive uptake by ionic salts.

5. Minimized Side Effects:
   avoids excess mineral loads associated with ionic salts, reducing the risk of hypernatremia, hyperkalemia, or gastrointestinal discomfort;
   beneficial for long-term use in individuals sensitive to mineral imbalances.

6. Multifunctional Therapeutics:
   covalent bonds integrate the effects of beta-hydroxybutyrate and amino acids, creating multifunctional compounds for broader applications (e.g., neuroprotection and muscle synthesis).

In some implementations, R-beta-hydroxybutyrate may be utilized rather than other chiralities since R-beta-hydroxybutyrate may be more easily bound to leucine, purine, lysine, and/or other amino acids. Administration of beta-hydroxy butyrate or acetoacetate that is complexed with or coupled to an amino acid may reduce the intake of cations associated with beta-hydroxybutyrate or acetoacetate salts (e.g., which may inhibit side effects associated with administration) and/or allow administration of another compound that has health benefits (e.g., administration of some amino acid may promote smooth muscle growth and/or cell repair, including muscle repair). In some implementations, approximately 0.5 g to approximately 10 g of amino acid may be administered with a beta-hydroxybutyrate. For example, less than approximately 50 g of R-beta-hydroxybutyrate, acetoacetate, or ketone body precursor and less than approximately 60 mg of an amino acid, such as leucine, may be administered daily. In some implementations, approximately 0.5 g to approximately 2 g of an amino acid, such as leucine, may be administered with a beta-hydroxybutyrate, acetoacetate, or ketone body precursor. For example, approximately the composition administered may include approximately 0.1 g to approximately 7 g of R-beta-hydroxybutyrate, acetoacetate, or ketone body precursor and approximately 1-3 g of leucine. The R-beta-hydroxybutyrate, acetoacetate, or ketone body precursor and the leucine may be a mixture, administered separately and proximate in timing, a complex, and/or administered in any other appropriate manner.

In some implementations, the composition may include R-beta-hydroxybutyrate salt and beta-hydroxybutyrate-amino acid complex or compound (e.g., beta-hydroxybutyrate bound to amino acid, such as R-beta-hydroxybutyrate-leucine complex or compound). For example, an individual may be administered a first weight amount of sodium beta-hydroxybutyrate and a second weight amount of beta-hydroxybutyrate amino-acid complex or compound. The first amount and the second amount may be different or the same. Acetoacetate and ketone body precursors can be similarly administered.

In some implementations, the beta-hydroxybutyrate or acetoacetate composition may include beta-hydroxybutyrate or acetoacetate salt and beta-hydroxybutyrate or acetoacetate esters. For example, an individual may be administered a first weight amount of sodium beta-hydroxybutyrate or acetoacetate and a second weight amount of beta-hydroxybutyrate or acetoacetate ester. The first amount and the second amount may be different or the same. The beta-hydroxybutyrate or acetoacetate salt and the beta-hydroxybutyrate or acetoacetate ester may be a bound complex, a mixture of compounds, and/or separately administered approximately concurrently. In some implementations, the beta-hydroxybutyrate ester may be in powdered form (e.g., plated beta-hydroxybutyrate ester), liquid and/or gel form. The combination of beta-hydroxybutyrate or acetoacetate salt and beta-hydroxybutyrate or acetoacetate ester during administration may allow less salt to be utilized while producing a result (e.g., weight maintenance and/or loss; enhanced and/or maintained ketosis; elevated blood ketone levels; blood glucose reduction and/or maintenance; increase in energy; increase in mood; increase in performance; and/or increase in cognitive function). In some implementations, elevated ketone levels (e.g., elevated blood ketone levels) may increase energy, mood, performance, and/or cognitive function in users. For example, the administration of the first amount of beta-hydroxybutyrate salt may cause a first level of blood ketone level, which may be maintained by processing of the second amount of the beta-hydroxybutyrate ester (e.g., as the body of the individual processes the beta-hydroxy butyrate ester the level of beta-hydroxy butyrate in the blood, and thus blood ketone level, may also increase over time to enhance and/or maintain the initial elevation caused by of the administered beta-hydroxybutyrate or acetoacetate salt).

For example, a ratio of beta-hydroxybutyrate or acetoacetate to beta-hydroxybutyrate or acetoacetate ester may be approximately 1 beta-hydroxybutyrate or acetoacetate salt: approximately 1 beta-hydroxybutyrate or acetoacetate ester to approximately 1 beta-hydroxybutyrate or acetoacetate salt: approximately 20 beta-hydroxybutyrate or acetoacetate ester. The ratio of beta-hydroxybutyrate or acetoacetate to beta-hydroxybutyrate or acetoacetate ester may be approximately 20 beta-hydroxybutyrate or acetoacetate salt: approximately 1 beta-hydroxybutyrate or acetoacetate ester to approximately 1 beta-hydroxybutyrate or acetoacetate salt: approximately 20 beta-hydroxybutyrate or acetoacetate ester. In some implementations, a ratio of beta-hydroxybutyrate or acetoacetate to beta-hydroxybutyrate or acetoacetate ester may be approximately 1 beta-hydroxybutyrate or acetoacetate salt: approximately 1 beta-hydroxybutyrate or acetoacetate ester to approximately 1 beta-hydroxybutyrate or acetoacetate salt: approximately 5 beta-hydroxybutyrate or acetoacetate ester.

Related compounds that may be included as beta-hydroxybutyrate or acetoacetate in the composition may include derivatives of beta-hydroxybutyrate or acetoacetate, include esters of (R)-3-hydroxybutyrate or acetoacetate and oligomers of (R)-3-hydroxybutyrate. For example, beta-hydroxybutyrate or acetoacetate esters derived from alcohols, such as altrose, arabinose, dextrose, erythrose, fructose, galactose, glucose, glycerol, gulose, idose, lactose, lyxose, mannose, ribitol, ribose, ribulose, sucrose, talose, threose, xylitol, xylose, galactosamine, glucosamine, mannosamine, N-acetylglucosamine, mannitol, sorbitol, threitol, (S)-1,2-propanediol and/or (R)-1,3-butanediol. In some implementations, a derivative of the beta-hydroxybutyrate or acetoacetate may include structures of (R)-3-hydroxybutyric acid and an exemplary ester thereof (a glycerol monoester). The R chirality of the derivatives may be selected for inclusion in the composition in some implementations (e.g., to deliver R-beta-hydroxybutyrate with the administration of the compound).

In some implementations, butyrate, beta-hydroxybutyrate (e.g., R-beta-hydroxybutyrate), acetoacetate, 1,3-butandiol, medium chain fatty acid, related compounds, and/or combinations thereof may be administered along with one or more additional compounds. The additional compounds may or may not be capable of independently increasing ketone levels, maintaining ketone levels, inducing ketosis, and/or maintaining ketosis. For example, additional compounds capable of independently increasing blood ketone levels may include short chain fatty acids (e.g., fatty acid with between 2 carbons than 6 carbons), short chain triglycerides (e.g., triglycerides with less than 6 carbons), medium chain fatty acids (e.g., fatty acid with 6-12 carbons), medium chain triglycerides (e.g., triglycerides with 7-12 carbons), long chain fatty acids (e.g., fatty acids with more than 12 carbons), long chain triglycerides (e.g., triglycerides with more than 12 carbons), and/or combinations thereof. In some implementations, short chain fatty acids and/or triglycerides may include acetate, propionate, and/or butyrate. Medium chain fatty acids and/or triglycerides may include lauric acid and/or coconut oil, coconut milk powder, fractionated coconut oil, isolated hexanoic acid, isolated octanoic acid, isolated decanoic acid, ethoxylated triglyceride, triglyceride derivatives thereof, aldehyde triglyceride derivatives thereof, monoglyceride derivatives thereof, diglyceride derivatives thereof, triglyceride derivatives thereof, and/or alkyl esters thereof. Long chain fatty acids and/or triglycerides may include dairy products and/or palm oil. In some implementations, a composition including R-beta-hydroxybutyrate and an additional compound that is independently capable of increasing ketone levels may increase ketone levels greater than merely the capability of each component individually (e.g., greater than an additive increase).

For example, the composition may include R-beta-hydroxybutyrate and an additional compound independently capable of increasing ketone levels such as caffeine. In some implementations, the composition may include approximately 0.5 g to approximately 50 g of R-beta-hydroxybutyrate, acetoacetate, or ketone body precursor and caffeine. In some implementations, the composition may include approximately 0.5 g to approximately 15 g of R-beta-hydroxybutyrate, acetoacetate, or ketone body precursor and less than approximately 500 mg of caffeine. In some implementations, the composition may include approximately 0.5 g to approximately 15 g of R-beta-hydroxybutyrate, acetoacetate, or ketone body precursor and approximately 5 mg to approximately 500 mg of caffeine. In some implementations, the composition may include approximately 0.5 g to approximately 15 g of R-beta-hydroxybutyrate, acetoacetate, or ketone body precursor and approximately 10 mg to approximately 150 mg of caffeine. In some implementations, the composition may include approximately 0.5 g to approximately 15 g of R-beta-hydroxybutyrate, acetoacetate, or ketone body precursor and approximately 10 mg to approximately 50 mg of caffeine. The composition with R-beta-hydroxybutyrate, acetoacetate, or ketone body precursor (e.g., R-beta-hydroxybutyrate including at least one R-beta-hydroxybutyrate salt) and caffeine may increase and or maintain ketosis, weight loss, fat loss, and/or mental acuity. In some implementations, the composition with R-beta-hydroxybutyrate, acetoacetate, or ketone body precursor (e.g., R-beta-hydroxybutyrate or acetoacetate including at least one R-beta-hydroxybutyrate or acetoacetate salt) and caffeine may increase mental processes (e.g., acuity including cognitive functioning, mood, energy, alertness, focus, performance, effects of aging, etc.); improve and/or maintain body composition; function as a therapeutic for one or more of the described conditions or disorders (e.g., treat neurological disorders); and/or combinations thereof.

In some implementations, the composition may include R-beta-hydroxybutyrate, acetoacetate, or ketone body precursor (e.g., 1,3-butandiol or medium chain fatty acid) and an additional compound independently capable of increasing ketone levels, such as 1,3,7,9-tetramethyluric acid (commercially available as theacrine; and/or commercially available as TeaCrine® from Compound Solutions, California, USA). In some implementations, the composition may include approximately 0.5 g to approximately 15 g of R-beta-hydroxybutyrate, acetoacetate, or ketone body precursor and less than approximately 500 mg of 1,3,7,9-Tetramethyluric acid. In some implementations, the composition may include approximately 5 g to approximately 15 g of R-beta-hydroxybutyrate, acetoacetate, or ketone body precursor and less than approximately 500 mg of 1,3,7,9-tetramethyluric acid.

For example, a pharmaceutically effective amount of one or more short chain fatty acids and/or one or more short chain triglycerides (e.g., butyric acid and/or butyrate) may be administered with a pharmaceutically effective amount of beta-hydroxybutyrate. In some implementations, approximately 1 g to approximately 10 g of beta-hydroxybutyrate, acetoacetate, or ketone body precursor and approximately 0.1 g to approximately 50 g of short chain fatty acid and/or triglyceride may be administered from once a day to approximately 5 times a day. In some implementations, approximately 1 g to approximately 3 g of beta-hydroxybutyrate, acetoacetate, or ketone body precursor and approximately 1 g of short chain fatty acid and/or triglyceride may be administered from once a day to approximately 5 times a day. In some implementations, the short chain fatty acid and/or triglyceride may include butyrate or derivatives of butyrate. Butyrate and/or derivatives of butyrate may be administered with and/or without beta-hydroxybutyrate to manage metabolic conditions, such as ketosis, and/or for other appropriate therapeutic purposes. Administered butyrate may be converted to beta-hydroxybutyrate in humans, and thus may increase the amount of beta-hydroxybutyrate delivered to the user. In some implementations, administration of butyrate, beta-hydroxybutyrate, acetoacetate, or ketone body precursor may promote hGH synthesis, improve basal and GHRH-induced hGH-secretion, increase muscle fiber cross-sectional area, inhibit intramuscular fat accumulation; reduce fat mass in a user; improve glucose metabolism; increase markers of mitochondrial biogenesis in skeletal muscle and/or whole-body oxygen consumption; reduced markers of oxidative stress and apoptosis and altered antioxidant enzyme activity; cause butyrate enhanced intracellular free cytosolic calcium levels (e.g., by acting through GPR41 and 43); increase beta-hydroxybutyrate levels; and/or support barrier function(s) in the gut and/or reduce inflammation associated with ulcerative colitis. Since butyrate is processed by the body to provide beta-hydroxybutyrate, the delivery of beta-hydroxybutyrate via the butyrate may supplement the directly administered beta-hydroxybutyrate to maintain a level of beta-hydroxy-butyrate in the blood (e.g., to promote ketosis, weight loss and/or management, etc.).

However, butyrate and/or butyric acid may not be palatable to individuals (e.g., since the odor and taste are often compared to vomit). Thus, in some implementations, butyrate and/or beta-hydroxybutyrate (e.g., R-beta-hydroxy-butyrate), acetoacetate, or ketone body precursor may be processed to reduce organoleptic reactions. For example, the butyrate and/or beta-hydroxybutyrate (e.g., R-beta-hydroxy-butyrate), acetoacetate, or ketone body precursor may be encapsulated, microemulsion, liposomes, agglomeration, masking/flavoring technologies, and/or otherwise processed as appropriate to reduce organoleptic reactions from individuals administered the described composition(s). In some implementations, microencapsulated butyrate, beta-hy-droxybutyrate, acetoacetate, or ketone body precursor, and/or butyric acid may be utilized (e.g., in combination with beta-hydroxybutyrate). Using microencapsulated butyrate, beta-hydroxybutyrate, acetoacetate, or ketone body precur-sor, and/or butyric acid (e.g., when compared with using unencapsulated forms) may increase individual satisfaction and/or compliance with an administration schedule since odor from the butyrate and/or butyric acid may be reduced and/or removed. The microencapsulated butyrate, beta-hy-droxybutyrate, acetoacetate, or ketone body precursor, and/or butyric acid may be a free-flowing granular powder; dispersible in water; stable in acidic water solution for 30 minutes; allow controlled release in stomach and/or small intestines; inhibit glucose response (e.g., to any added materials); and/or allow delivery of a high butyrate content (e.g., around 70%).

In some implementations, a pharmaceutically effective amount of butyrate may be administered via triglyceride tributyrin (e.g., glyceryl tributyrate or tributyrin). The butyrate via triglyceride tributyrin may be administered separately and/or in conjunction with one or more of the other described compounds (e.g., beta-hydroxybutyrate, acetoacetate, ketone body precursor, fatty acids and/or esters, etc.). For example, up to approximately 200 mg/kg of the individual may be administered (e.g., up to 3 times daily). Administration of the tributyrin may allow a delayed release of butyrate to the body as the tributyrin is processed by the body of the individual. The tributyrin may be unencapsulated and/or encapsulated (e.g., microencapsulated).

In some implementations, administration of beta-hy-droxybutyrate, acetoacetate, or ketone body precursor and a short chain compound (e.g., short chain fatty acid and/or short chain triglyceride) may unexpectedly increase beta-hydroxybutyrate and acetoacetate concentrations in the blood more than the administration of similar amounts of beta-hydroxybutyrate and medium chain compounds (e.g., short chain fatty acid and/or short chain triglyceride) and/or may increase beta-hydroxybutyrate concentrations in the blood more than each component individually.

In some implementations, a pharmaceutically effective amount of beta-hydroxybutyrate, acetoacetate, or ketone body precursor may be administered with a pharmaceutically effective amount of long chain fatty acid and/or tri-glyceride. For example, 0.1-50 g of beta-hydroxybutyrate, acetoacetate, or ketone body precursor and 0.1 to 50 g of long chain fatty acid may be administered to an individual between 1-5 times a day. In some implementations, approximately 1 g to approximately 3 g of beta-hydroxybutyrate, acetoacetate, or ketone body precursor and approximately 1 g of long chain fatty acid and/or triglyceride may be administered from once a day to approximately 5 times a day.

In some implementations, beta-hydroxybutyrate, acetoacetate, or 1,3-butanediol, short chain compound(s) (e.g., fatty acids and/or triglycerides, butyrate), and/or medium chain compound(s) (e.g., fatty acids and/or triglycerides) may be administered approximately simultaneously and/or sequentially to an individual. For example, approximately 0.1 g to approximately 50 g beta-hydroxybutyrate, acetoacetate, or 1,3-butanediol, approximately 0.1 g to approximately 50 g short chain triglyceride, and approximately 0.1 g to approximately 50 g medium chain fatty acid such as lauric acid and/or coconut oil may be administered between 1-5 times a day. In some implementations, approximately 1 g to approximately 3 g of beta-hydroxybutyrate, acetoacetate, or 1,3-butanediol and approximately 1 g of short chain fatty acid and/or triglyceride and/or approximately 1 g of medium chain fatty acid and/or triglyceride may be administered from once a day to approximately 5 times a day. In some implementations, approximately 0.1 g to approximately 20 g beta-hydroxybutyrate, acetoacetate, or 1,3-butanediol (e.g., salts, esters, isomers, and/or other appropriate forms) may be administered in humans. In some implementations, approximately 0.1 g to approximately 20 g butyrate may be administered in humans.

In some implementations, other compounds, such as compounds capable of independently decreasing glucose levels, may be administered with beta-hydroxybutyrate, such as berberine and/or associated metabolites (e.g., dihy-droberberine and/or tetrahydroberberine). U.S. patent application Ser. No. 15/491,933 entitled "ADMINISTRATION OF DIHYDROBERBERINE" to Lowery et al, filed Apr. 19, 2017, and U.S. Provisional Patent Application No. 62/324, 794, entitled "ADMINISTRATION OF DIHYDROBER-BERINE" to Lowery et al, filed Apr. 19, 2016, describe dihydroberberine administration with ketone sensitizers such as beta-hydroxybutyrate, and is hereby fully incorporated herein. In some implementations, one or more beta-hydroxybutyrates and/or other compounds described herein may be utilized as a ketone sensitizer with the dihydrober-berine.

In some implementations, directly administering beta-hydroxybutyrate, acetoacetate, or ketone body precursor plus another compound that is processed to deliver beta-hydroxybutyrate (e.g., beta-hydroxybutyrate, acetoacetate, or 1,3-butanediol ester, beta-hydroxybutyrate polymer, butyrate, other appropriate compounds, and/or combinations thereof) over time may allow a first level of beta-hydroxy-butyrate or acetoacetate in the blood to be maintained over a period of time. For example, since the directly administered beta-hydroxybutyrate may elevate blood beta-hy-droxybutyrate levels to a first concentration and this concentration may be approximately maintained over a period of time by providing additional beta-hydroxybutyrate via another compound administered approximately concurrently (e.g., short chain fatty acid and/or triglyceride, beta-hydroxybutyrate ester, beta-hydroxybutyrate polymer, beta-hydroxybutyrate amino acid complex or compound, etc.), acetoacetate, or 1,3-butanediol, or medium chain fatty acid or ester.

In some implementations, one or more other compounds may be administered (e.g., included in the composition and/or separately administered) with the butyrate (e.g., microencapsulated butyrate), beta-hydroxybutyrate (e.g., R-beta-hydroxybutyrate), acetoacetate, or ketone body precursor and/or fatty acids or esters, such as short chain fatty acids. Other compositions may include, but are not limited to amino acids, amino acid metabolites, vitamins, minerals, coconut milk powder, flavorings, colorings, binders, electrolytes, tetrahydrobiopterin, nucleic acids, alpha-ketoglu-taric acid, alpha lipoic acid, nutritional co-factors, beta-methyl-beta-hydroxybutyrate, arginine alpha-ketoglutarate, R-alpha lipoic acid, thiamine, NAD+, NADH, riboflavin, FAD+, FADH, riboflavin-5-phosphate, niacin, nicotinic acid, niacinamide, inositol hexanicotinate, pyridoxine, pyri-doxal, pyridoxamine, ascorbic acid and ascorbate salts, citric acid, malic acid, sodium benzoate, pyridoxal-5-phosphate, methylcobalamin, cyanocobalamin, adenosylcobalamin, hydroxycobalamin, pantothenic acid, pantetheine, potas-sium sorbate, acesulfame K, aspartame, sucralose, stevia, monk fruit extract, allulose, prebiotic fibers, xylo-oligosac-charides (XOS), galacto-oligosaccharides (GOS), mannan-oligosaccharides (MOS), isomalto-oligosaccharides (IMO), lipo-oligosaccharides (LOS), xanthan gum, and other organic gums/thickeners/suspension agents, and combina-tions thereof.

In various implementations, administration of a compo-sition that includes beta-hydroxybutyrate, acetoacetate, or ketone body precursor may improve the health of an indi-vidual. R-beta-hydroxybutyrate may be capable of providing a greater impact on the health of an individual than D,L-beta-hydroxybutyrate and/or L-beta-hydroxybutyrate. Although previously unknown, L-beta-hydroxybutyrate may decrease the effectiveness of R-beta-hydroxybutyrate with respect to at least a portion of the impact on health. With respect to some impacts on health, L-beta-hydroxybu-tyrate may have no impact on health. In some implementa-tions, even double the amount of D,L-beta-hydroxybutyrate may not achieve some of the same results (e.g., in health improvement) as R-beta-hydroxybutyrate. Thus, unexpect-edly administration of D,L-beta-hydroxybutyrate rather than R-beta-hydroxybutyrate may not have the same impact on health and/or have less of an impact on health of an individual. For example, administration of a composition that includes R-beta-hydroxybutyrate (e.g., and/or other compounds) may improve and/or maintain an individual's health.

Administration of R-beta-hydroxybutyrate, acetoacetate, or ketone body precursor as described may increase lifespan in individuals following a dietary plan (e.g., standard Ameri-can low-fat, ketogenic, Palco, Mediterranean, etc.) and/or not following a dietary plan. For example, approximately 10 g of R-beta-hydroxybutyrate, acetoacetate, or ketone body precursor to approximately 30 g R-beta-hydroxybutyrate, acetoacetate, or ketone body precursor may be administered to increase lifespan. In some implementations, other appro-priate amounts of R-beta-hydroxybutyrate, acetoacetate, or ketone body precursor may be included in the composition.

In some implementations, administration of R-beta-hy-droxybutyrate, acetoacetate, or ketone body precursor may treat and/or lessen the impact of symptoms of disease(s) and/or disorders, such as diseases that impact cognitive function. Administration of R-beta-hydroxybutyrate, acetoacetate, or ketone body precursor may increase motor function in individuals with Parkinson's disease. For example, approximately 5 g of R-beta-hydroxybutyrate, acetoacetate, or ketone body precursor to approximately 15 g R-beta-hydroxybutyrate, acetoacetate, or ketone body pre-cursor may be administered to increase motor function. In some implementations, other appropriate amounts of R-beta-hydroxybutyrate, acetoacetate, or ketone body pre-cursor may be included in the composition.

Administration of R-beta-hydroxybutyrate, acetoacetate, or ketone body precursor may increase fat loss. Unlike with conventional diets, in which weight loss often comes from decreases in water retention and/or muscle mass, administration of R-beta-hydroxybutyrate, acetoacetate, or ketone body precursor may cause decreases in fat loss (see for example, Figure SB). In addition, administration of R-beta-hydroxybutyrate may decrease levels of LPL in the body, and thus reduce or inhibit fat storage and/or encourage existing fat storage utilization by the body. For example, approximately 1 g of R-beta-hydroxybutyrate, acetoacetate, or ketone body precursor to approximately 20 g R-beta-hydroxybutyrate, acetoacetate, or ketone body precursor may be administered to cause fat loss and/or reduce fat storage. In some implementations, other appropriate amounts of R-beta-hydroxybutyrate, acetoacetate, or ketone body precursor may be included in the composition. Admin-istration of R-beta-hydroxybutyrate, acetoacetate, or ketone body precursor may allow fat loss greater than 5 kg while maintaining lean mass. In some implementations, the admin-istration of R-beta-hydroxybutyrate, acetoacetate, or ketone body precursor increases the amount of fat used as fuel.

In some implementations, administration of R-beta-hy-droxybutyrate, acetoacetate, or ketone body precursor may improve and/or maintain health markers such as C-reactive protein and/or fasting glucose. Administration of R-beta-hydroxybutyrate, acetoacetate, or ketone body precursor may decrease inflammation (e.g., as shown by C-reactive protein levels). Administration of R-beta-hydroxybutyrate may decrease fasting glucose. For example, approximately 3 g of R-beta-hydroxybutyrate, acetoacetate, or ketone body precursor to approximately 20 g R-beta-hydroxybutyrate, acetoacetate, or ketone body precursor may be administered to cause a reduction in and/or maintain a low fasting glucose. In some implementations, other appropriate amounts of R-beta-hydroxybutyrate, acetoacetate, or ketone body precursor may be included in the composition. In some implementations, R-beta-hydroxybutyrate, acetoacetate, or ketone body precursor may be administered with one or more other compounds to decrease glucose levels and/or sensitivity. For example, administration of a composition of R-beta-hydroxybutyrate, acetoacetate, or ketone body pre-cursor and a berberine, such as dihydroberberine, may cause, reduce and/or maintain low fasting glucose. Administration of a composition of R-beta-hydroxybutyrate, acetoacetate, or ketone body precursor and a berberine, such as dihyd-roberberine, may cause reduce and/or maintain low glucose levels. In some implementations, less than approximately 15 g of R-beta-hydroxybutyrate, acetoacetate, or ketone body precursor may be administered with less than approximately 600 mg of dihydroberberine.

Administration of R-beta-hydroxybutyrate, acetoacetate, or ketone body precursor may decrease ketone levels (see e.g., FIGS. 11A and 11B). Decreasing blood ketone levels may increase weight loss, maintain weight loss, improve performance, increase mental acuity, and/or have other health improvement and health maintenance features. For example, even at levels less than 10 g (e.g., approximately 5 g), administration of R-beta-hydroxybutyrate, acetoac-etate, or ketone body precursor may decrease ketone levels while L-beta-hydroxybutyrate does not, and D,L-beta-hy-droxybutyrate does not to the same extent. R-beta-hydroxy-butyrate, acetoacetate, or ketone body precursor may increase blood ketone levels 5 times as much as similar administration amounts of D,L-beta-hydroxybutyrate. By being able to decrease an amount of R-beta-hydroxybu-tyrate, acetoacetate, or ketone body precursor (e.g., when compared with administering D,L-beta-hydroxybutyrate) administered and achieve the same results, a decrease in an amount cation (e.g., sodium, potassium, etc.) may also be administered. Since some individuals may prefer and/or may not tolerate higher dosages of the cations of the R-beta-hydroxybutyrate salt, utilizing R-beta-hydroxybutyrate, acetoacetate, or ketone body precursor may allow administration to more people, increase user satisfaction, and/or decrease side effects (e.g., associated with additional consumption of these cations). In some implementations, approximately 0.1 g of R-beta-hydroxybutyrate, acetoacetate, or ketone body precursor to approximately 10 g R-beta-hydroxybutyrate, acetoacetate, or ketone body precursor may be administered to increase blood ketone levels. Approximately 0.5 g of R-beta-hydroxybutyrate, acetoacetate, or ketone body precursor to approximately 3 g R-beta-hydroxybutyrate, acetoacetate, or ketone body precursor may be administered to maintain blood ketone levels. In some implementations, other appropriate amounts of R-beta-hydroxybutyrate, acetoacetate, or ketone body precursor may be included in the composition.

Administration of R-beta-hydroxybutyrate, acetoacetate, or ketone body precursor may increase performance and decrease perceived exertion (e.g., as opposed to when administered D,L-beta-hydroxybutyrate). For example, approximately 3 g of R-beta-hydroxybutyrate, acetoacetate, or ketone body precursor to approximately 15 g R-beta-hydroxybutyrate, acetoacetate, or ketone body precursor may be administered to increase performance and/or decrease perceived exertion. In some implementations, other appropriate amounts of R-beta-hydroxybutyrate, acetoacetate, or ketone body precursor may be included in the composition.

In various implementations, oral administration of R-beta-hydroxybutyrate, acetoacetate, or ketone body precursor may increase muscle protein synthesis while D,L-beta-hydroxybutyrate does not increase muscle protein synthesis. For example, approximately 10 g of R-beta-hydroxybutyrate, acetoacetate, or ketone body precursor to approximately 30 g R-beta-hydroxybutyrate, acetoacetate, or ketone body precursor may be administered to increase muscle protein synthesis. In some implementations, other appropriate amounts of R-beta-hydroxybutyrate, acetoacetate, or ketone body precursor may be included in the composition.

Figure 13A:
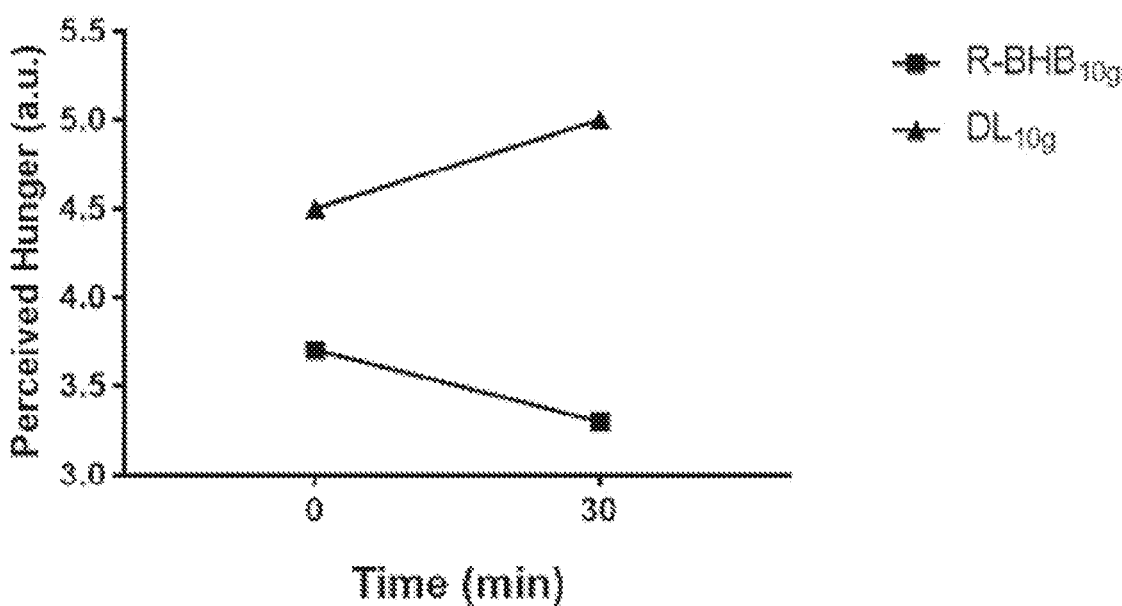
FIG. 13A illustrates a chart illustrating perceived hunger following an implementation of an example administration protocol.
Figure 13B:
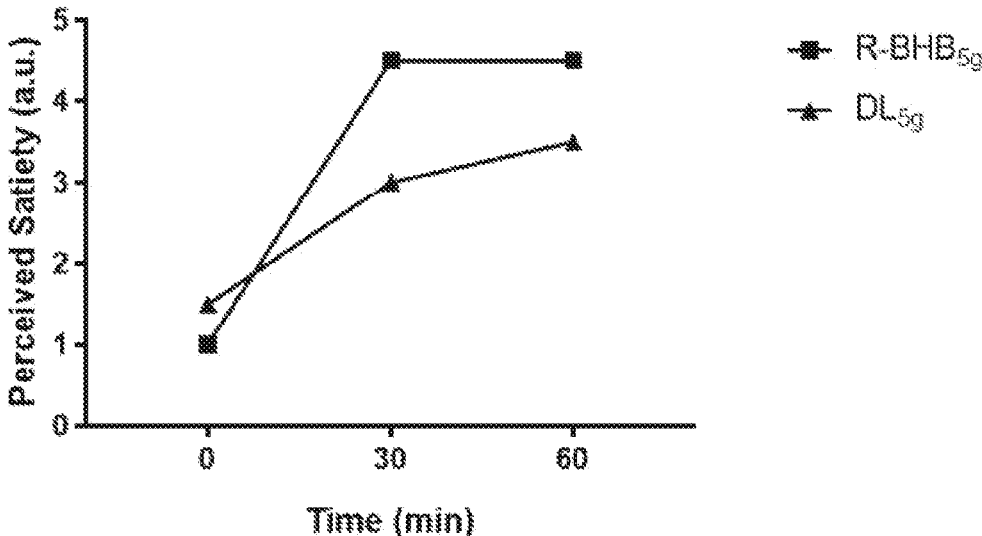
FIG. 13B illustrates a chart illustrating perceived satiety following an implementation of an example administration protocol.

In some implementations, the administration of R-beta-hydroxybutyrate, acetoacetate, or ketone body precursor, unlike D,L-beta-hydroxybutyrate may decrease perceived hunger and/or increase satiety) which may inhibit overeating and thus promote weight loss (see e.g., FIGS. 13A and 13B). In some implementations, the administration of R-beta-hydroxybutyrate, acetoacetate, or ketone body precursor, unlike D,L-beta-hydroxybutyrate, may increase perceived energy (see e.g., FIG. 13C).

In some implementations, administration of R-beta-hydroxybutyrate, acetoacetate, or ketone body precursor increases mental acuity. For example, approximately 0.1 g of R-beta-hydroxybutyrate, acetoacetate, or ketone body precursor to approximately 10 g R-beta-hydroxybutyrate, acetoacetate, or ketone body precursor may be administered to increase mental acuity. In some implementations, other appropriate amounts of R-beta-hydroxybutyrate, acetoacetate, or ketone body precursor may be included in the composition.

In some implementations, the administration of R-beta-hydroxybutyrate may be supplemented with other forms of beta-hydroxybutyrate, butyric acid, and/or butyrate.

In some implementations, the composition administered may include R-beta-hydroxybutyrate, acetoacetate, or ketone body precursor. The amount of R-beta-hydroxybutyrate, acetoacetate, or ketone body precursor included in the composition may be selected to obtain a result (e.g., induce ketosis; maintain ketosis; increase ketone levels, mental acuity, strength, etc.) upon administration (e.g., a pharmaceutically effective amount may be administered at a dosage and/or over a predetermined time period). In some implementations, the dosage and/or frequency of dosage may vary over time (e.g., initial vs a lower dosage for maintenance, vary based on time of day, vary based on whether taken with or without a meal, etc.).

The R-beta-hydroxybutyrate, acetoacetate, or ketone body precursor in the composition may include any appropriate and/or appropriate number of forms, such as salts, derivatives (e.g., esters), polymers, and/or complexes with other compounds. For example, the composition may include R-beta-hydroxybutyrate or acetoacetate salt (e.g., sodium R-beta-hydroxybutyrate or acetoacetate, magnesium R-beta-hydroxybutyrate or acetoacetate, and/or potassium R-beta-hydroxybutyrate or acetoacetate) and/or another form of R-beta-hydroxybutyrate or acetoacetate (e.g., ester, polymer, complex, etc.). In some implementations, the composition may include an ester of R-beta-hydroxybutyrate or acetoacetate. The composition may include an amino acid (e.g., separate and/or complexed with or coupled to R-beta-hydroxybutyrate), such as leucine. The use of non-salt base R-beta-hydroxybutyrate or acetoacetate may increase user satisfaction (e.g., by reducing the cation, such as sodium and/or potassium, load due to ingestion of the composition; by decreasing side effects; etc.), increase the applicability of the administration (e.g., since users sensitive to the cations of the R-beta-hydroxybutyrate or acetoacetate salts may be less sensitive to the non-salt and/or lower salt plus non-salt forms of the composition). The administration of the composition may increase blood ketone levels, induce ketosis, maintain blood ketone levels, maintain ketosis, increase health, increase strength, increase mental acuity, etc. In some implementations, a first composition that includes R-beta-hydroxybutyrate or acetoacetate salt may be administered to cause a first impact (e.g., induce ketosis, quickly increase mental acuity, quickly increase strength, etc.) and a second composition that includes non-salts of R-beta-hydroxybutyrate or acetoacetate (e.g., esters, polymers, complexes, etc.) and/or lower levels of R-beta-hydroxybutyrate salt may be utilized to cause a second impact (e.g., maintain ketosis, maintain mental acuity, maintain increased strength, etc.).

In some implementations, the form(s) of R-beta-hydroxybutyrate or acetoacetate included in the composition administered may be selected based on the delivery form. For example, in some forms of food products the composition may include R-beta-hydroxybutyrate polymer (e.g., due to taste since increased cations like sodium may decrease palatability; due to nutrition since increased cations such as sodium may decrease nutrition; due to mixability, etc.). As another example, the composition may include R-beta-hydroxybutyrate or acetoacetate salts or other forms (e.g., microencapsulated) to provide quick-dissolve powders.

In various implementations, a composition may include R-beta-hydroxybutyrate. The R-beta-hydroxybutyrate may be in any appropriate form (e.g., salt, ester, polymer, complex, derivatives thereof, and/or combinations thereof). The composition may include one or more additional compounds or compositions. Additional compounds or composition(s) may be capable of independently increasing blood ketone levels (e.g., fatty acids or esters, berberine or berberine metabolites such as dihydroberberine, etc.). Additional compounds or composition(s) may be capable of independently decreasing blood glucose levels (e.g., berberine or berberine metabolites such as dihydroberberine). In some implementations, additional compounds may not be capable of independently increasing blood ketone levels and/or decreasing blood glucose levels (e.g., additives, flavorings, colorings, minerals, vitamins, binders, anti-caking agents, etc.). The composition may be administered in an effective amount to cause a predetermined health impact (e.g., predetermined level of ketosis, blood ketone level, mental acuity, strength increase, perceived energy, fat loss, weight loss, etc.). The composition may be administered to an individual in a predetermined amount and/or different amounts over an administration schedule. In some implementations, once a first criteria is satisfied (e.g., period of time, number of doses, predetermined health impact), the dosage amount may be altered. For example, first dose(s) of the composition may be administered to cause a predetermined health impact and additional lower dose(s) of the composition may be administered to maintain the predetermined health impact (e.g., caused in part by the first doses).

The composition may be administered in any appropriate delivery form (e.g., tablet; capsule; food products such as powdered products that can be mixed into food, mixed into beverages, and/or consumed directly; beverage product; etc.). The composition may be administered according to any appropriate schedule (e.g., periodic dosages, dosages as user desires, etc.). The administration schedule may inhibit administration that elevates blood ketone levels too high, decreases blood glucose levels too low, and/or causes an individual to consume a dosage that substantially elevates the risk of adverse and/or side effects, in some implementations.

In some implementations, the composition may include a long-acting component and/or be long-acting. For example, since the body digests polymers and/or esters of beta-hydroxybutyrate (e.g., R-beta-hydroxybutyrate), the delivery of R-beta-hydroxybutyrate may be slower than a digestion of a beta-hydroxybutyrate salt (e.g., R-beta-hydroxybutyrate salt). In some implementations, the composition may include a R-beta-hydroxybutyrate and a long acting R-beta-hydroxybutyrate form (e.g., polymer, ester, coated and/or processed form to provide slow release). In some implementations, a first dose(s) may include at least one non-long-acting form of beta-hydroxybutyrate and a second dose(s) may include at least one long-acting form of beta-hydroxybutyrate. The first dose(s) may be administered to cause a predetermined health impact and the second dose(s) may be administered to maintain the caused predetermined health impact. In some implementations, users may select the appropriate dose based on user preference and/or properties (e.g., a user on a ketogenic diet may chose the second dose since the user may already be in ketosis).

EXAMPLES

Example 1

Four (4) subjects were administered 10 g of sodium D,L-beta-hydroxybutyrate and their blood ketone level in mmol/dL was tested after administration, 30 minutes, 60 minutes, 90 minutes, 120 minutes, and 180 minutes after administration. Each subject was also subsequently studied after administration of 10 g of sodium R-beta-hydroxybutyrate and 5 g of sodium R-beta-hydroxybutyrate. As illustrated in FIG. 1, on average, administration of 5 mg of sodium R-beta-hydroxybutyrate produced approximately the same blood ketone level in a subject after 30 minutes, 60 minutes, 90 minutes, 120 minutes, and 180 minutes as 10 g of the sodium D,L-beta-hydroxybutyrate.

Example 2

Three subjects were administered 10 grams of medium chain triglycerides and 8 grams of beta-hydroxybutyrate and blood beta-hydroxybutyrate concentration was monitored over time. The same subjects were later administered 10 grams of short chain triglycerides and 8 grams of beta-hydroxy butyrate and blood beta-hydroxy butyrate concentration was monitored. FIG. 2 illustrates an average blood ketone concentration (mmol/L) for the subjects after administration, after 30 minutes, after 60 minutes, after 90 minutes, after 120 minutes, and after 180 minutes. As illustrated in FIG. 2, administration of the beta-hydroxybutyrate with a short chain compound (illustrated in red bars or the second bar in each set), such as short chain triglyceride, caused greater elevation of blood ketone levels than administration of a similar amount of medium chain compound (illustrated in the blue bars or first bar in each set) at least after administration, after 30, 60, 90 minutes, and 180 minutes. Thus, administration of short chain compounds (e.g., fatty acids and/or triglycerides) may unexpectedly allow a smaller weight amount, when compared to medium chain compounds, to be administered to produce the same result (e.g., blood ketone level, weight loss, weight management, etc.) and/or allow greater results (e.g., when compared with similar amount of medium chain compounds).

Example 3

Figure 3:
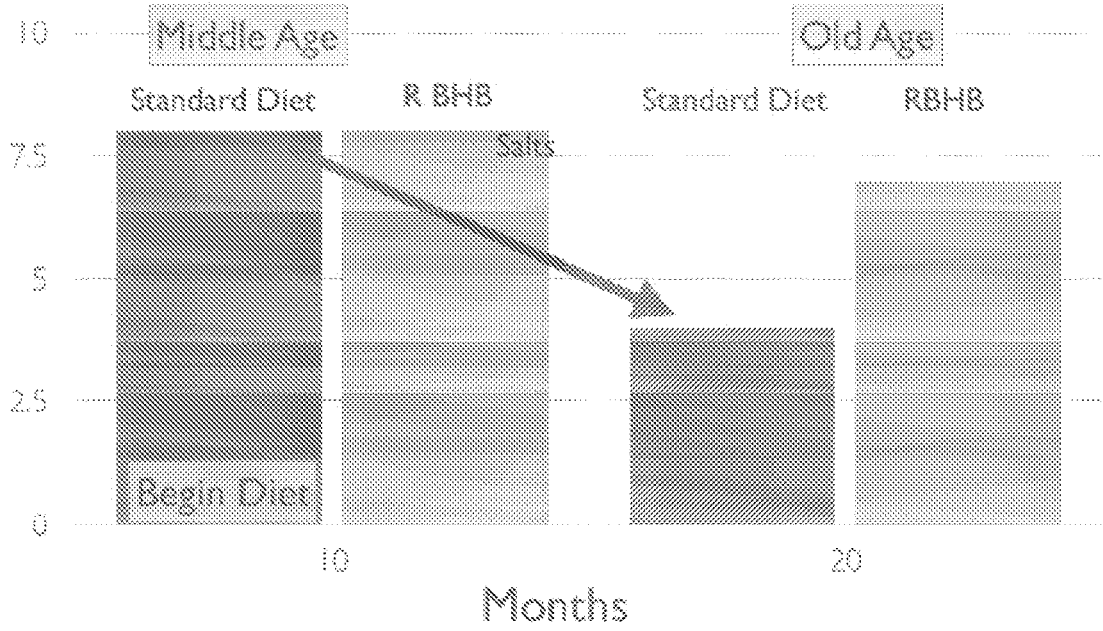
FIG. 3 illustrates a chart including lifespan of rats subject to an implementation of an administration of R-beta-hydroxybutyrate.

Sixteen rats (Fischer 344 rats) were studied for the effect of R-beta-hydroxybutyrate on lifespan. A first grouping of eight rats were fed an equivalent to a low-fat standard American diet and a second grouping of eight rats were fed the same equivalent to a low-fat standard American diet and supplemented with R-beta-hydroxybutyrate salt (e.g., sodium R-beta-hydroxybutyrate). The second grouping of rats were supplemented with the R-beta-hydroxybutyrate salt at middle age. FIG. 3 illustrates the average lifespans of the groupings of rats. As illustrated, at 20 months approximately half of the first grouping of rats died on the standard diet while only 12.5% of the second grouping of rats had died at 20 months. Thus, the supplementation of rat diets with R-beta-hydroxybutyrate increased lifespan in at least approximately 38.5% of the rats. Since the rat study was performed as an approximation of impact in humans, the addition of R-beta-hydroxybutyrate to a standard American low-fat diet may increase lifespan.

Example 4

An individual with Parkinson's disease was tested for motor function with and without administration of approximately 10 g of R-beta-hydroxybutyrate salt. The testing included a right-eye visual and motor performance apparatus to track motor function through eye movements.

Figure 4:
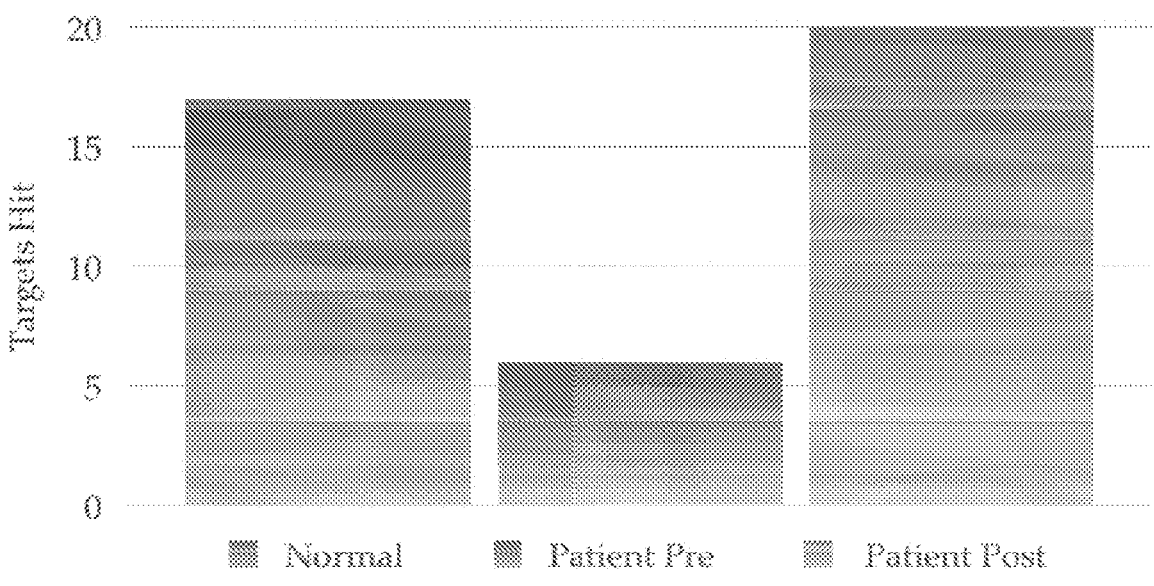
FIG. 4 illustrates a chart illustrating the results of motor skill testing following an implementation of an example administration protocol.

FIG. 4 is a chart illustrating the results of the motor skill testing following an example implementation of administration of R-beta-hydroxybutyrate. FIG. 4 illustrates average results for a similar non-Parkinson's population, the patient pre-administration of R-beta-hydroxybutyrate, and the patient post-administration of R-beta-hydroxybutyrate. As illustrated, the administration of R-beta-hydroxybutyrate increased motor function (e.g., approximately 30 minutes after administration of the R-beta-hydroxybutyrate).

Example 5

Figures 5A, 5B:
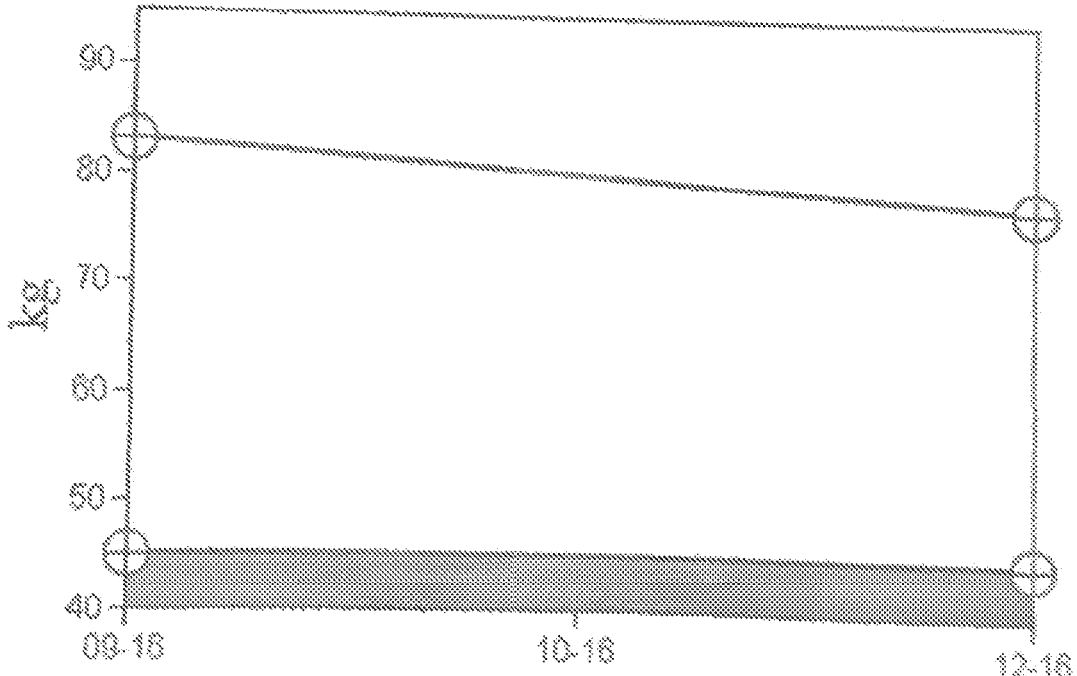
FIG. 5A illustrates a chart illustrating fat loss results following an implementation of an example administration protocol.
FIG. 5B illustrates a chart illustrating fat mass and lean mass results following an implementation of an example administration protocol.

An individual was administered 5 g of R-beta-hydroxybutyrate twice daily for 3 months. Xray absorptiometry was performed to determine the impact of the administration of R-beta-hydroxybutyrate on fat loss. FIG. 5A illustrates a chart that shows the results after 3 months of administration. As illustrated, the individual experienced a greater than approximately 10% decrease in fat mass. FIG. 5B illustrates that the fat loss was sustained while maintaining lean mass. Thus, the R-beta-hydroxybutyrate may cause weight loss through fat loss rather than lean mass (e.g., muscle mass).

Example 6

Figure 6:
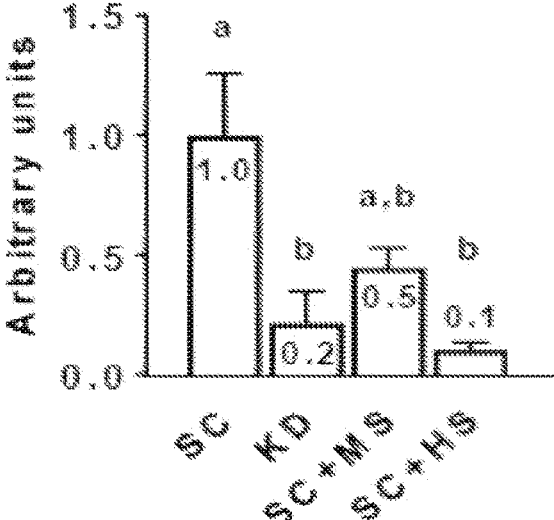
FIG. 6 illustrates a chart illustrating LPL levels in rats following an implementation of an example administration protocol.

A first grouping of 10 rats (labeled SC) were given a standard diet, a second grouping of 10 rats (labeled KD) were given a ketogenic diet, a third grouping of 10 rats (labeled SC+MS) were on the standard diet but given a first dosage of R-beta-hydroxybutyrate salt (e.g., equivalent to 5 g) and a fourth grouping was on the standard iet but given a second dosage of R-beta-hydroxybutyrate salt (e.g., equivalent to 10 g). FIG. 6 illustrates the average Lipoprotien lipase (LPL) in the rats. Since LPL is needed to transport fat into adipose tissue, lowering LPL levels would inhibit fat storage and encourage usage of fat storages. As illustrated, supplementation of a standard diet with even lower dosages of R-beta-hydroxybutyrate decreases LPL levels and thus inhibits fat storage.

Example 7

An individual with high C-reactive protein, which is associated with inflammation, was administered R-beta-hydroxybutyrate. After administration, the C-reactive protein levels were substantially reduced (e.g., 62.5 to 4.4). In addition, fasting glucose was decreased (e.g., 104 to 95).

Example 8

Figure 7:
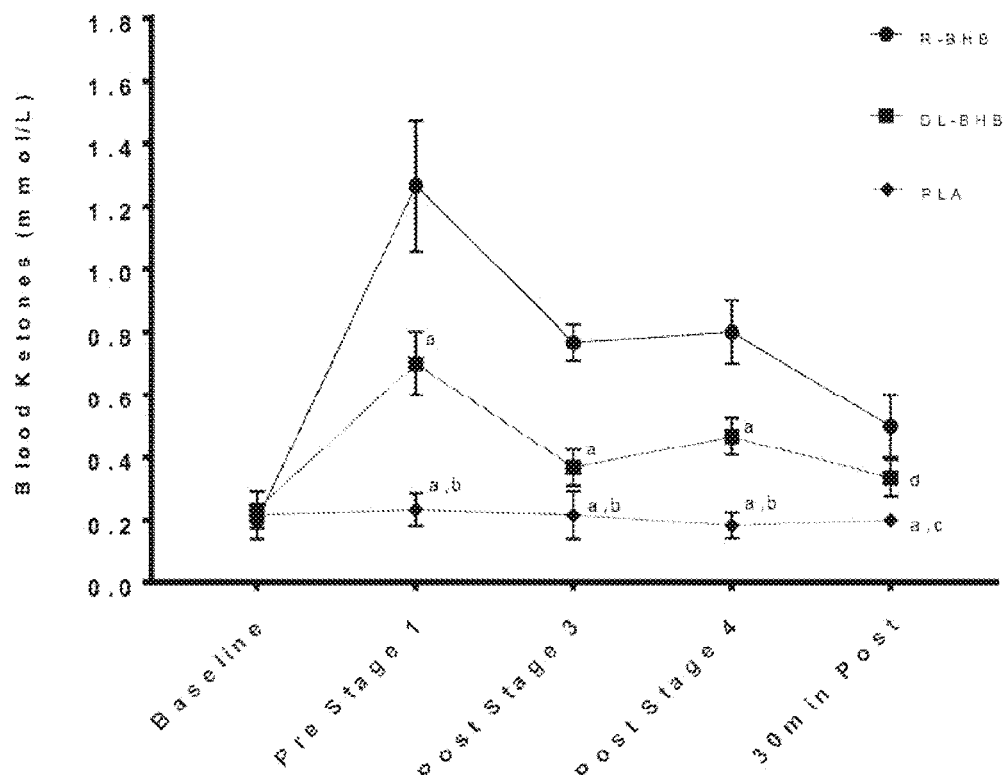
FIG. 7 illustrates a chart illustrating blood ketone levels following an implementation of an example administration protocol.
Figure 8:
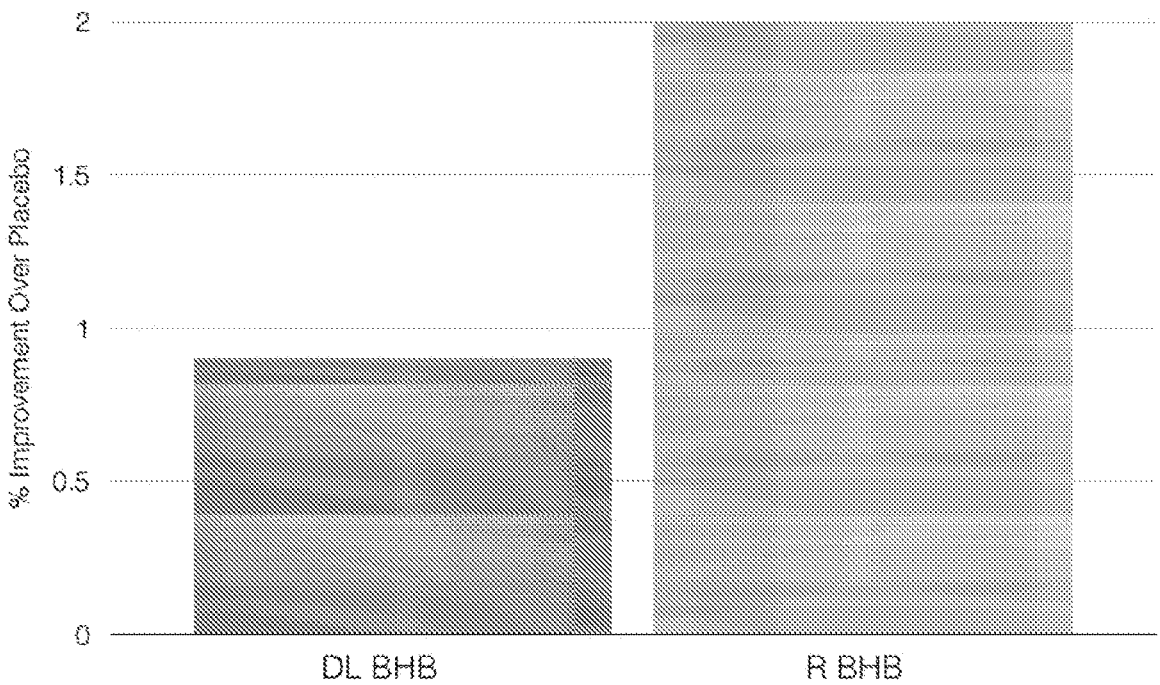
FIG. 8 illustrates a chart illustrating improvement over a placebo following an implementation of an example administration protocol.
Figure 9:
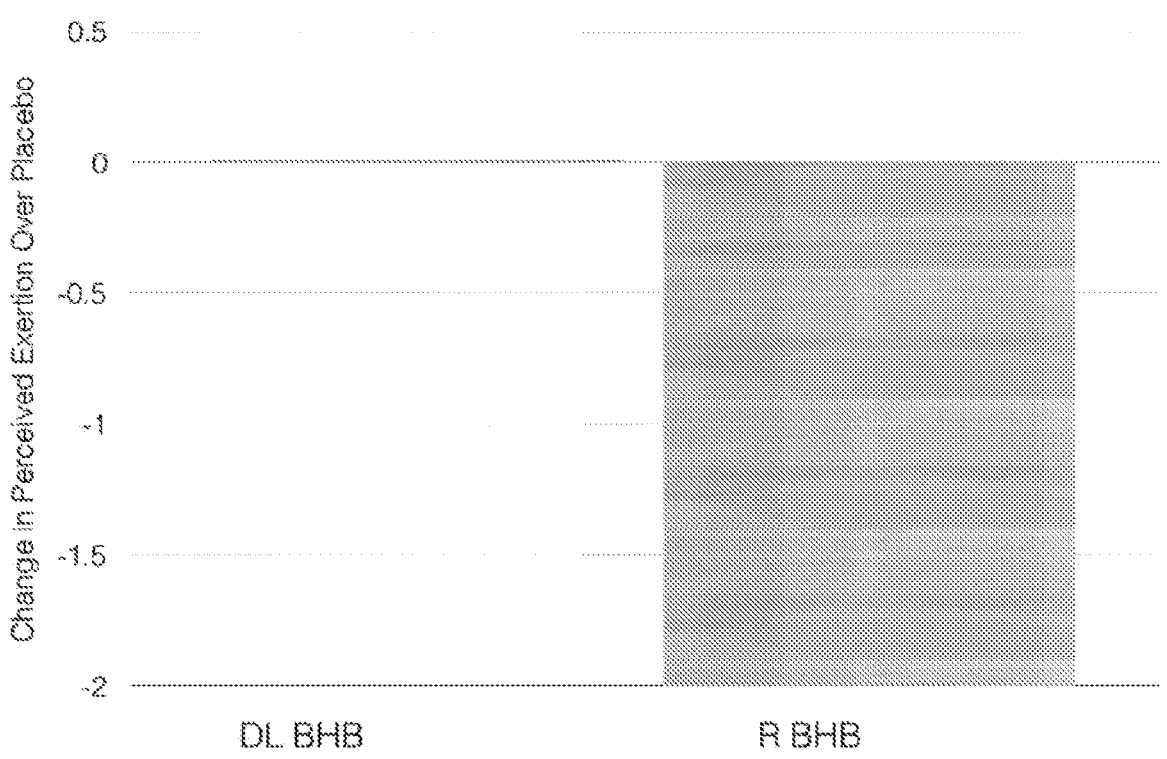
FIG. 9 illustrates a chart illustrating perceived exertion following an implementation of an example administration protocol.

Five healthy individuals were given a 2 km time test (e.g., 4 cycles of low to severely intense exercise on a wingate cycle ergometer) 30 minutes after administration of a placebo, 10 g of R-beta-hydroxybutyrate, and 10 g of R-beta-hydroxybutyrate. FIG. 7 illustrates the average blood ketone levels and FIG. 8 illustrates the percentage improvement over the administration of the placebo. As illustrated, blood ketone levels unexpectedly increased more than double during administration of R-beta-hydroxybutyrate when compared with administration of D,L-beta-hydroxybutyrate. In addition, performance (e.g., improvement in time) increased by more than double during administration of R-beta-hydroxybutyrate when compared with D,L-beta-hydroxybutyrate. FIG. 9 illustrates the perceived exertion experienced by the individuals. As illustrated, the individuals did not feel an impact in perceived exertion after administration with D,L-beta-hydroxybutyrate as compared with the perceived exertion improvement experienced after administration of R-beta-hydroxybutyrate. Thus, the R-beta-hydroxybutyrate has an unexpected impact on ketone levels and performance.

Example 9

Individuals were given a standard diet or ketogenic diet. Some individuals were administered R-beta-hydroxybutyrate (e.g., 10 g). R-beta-hydroxybutyrate was able to numerically increase superoxide dismutase 2 levels (SOD) in the brain which indicates greater antioxidant capacity in the brain.

Example 10

Figure 10:
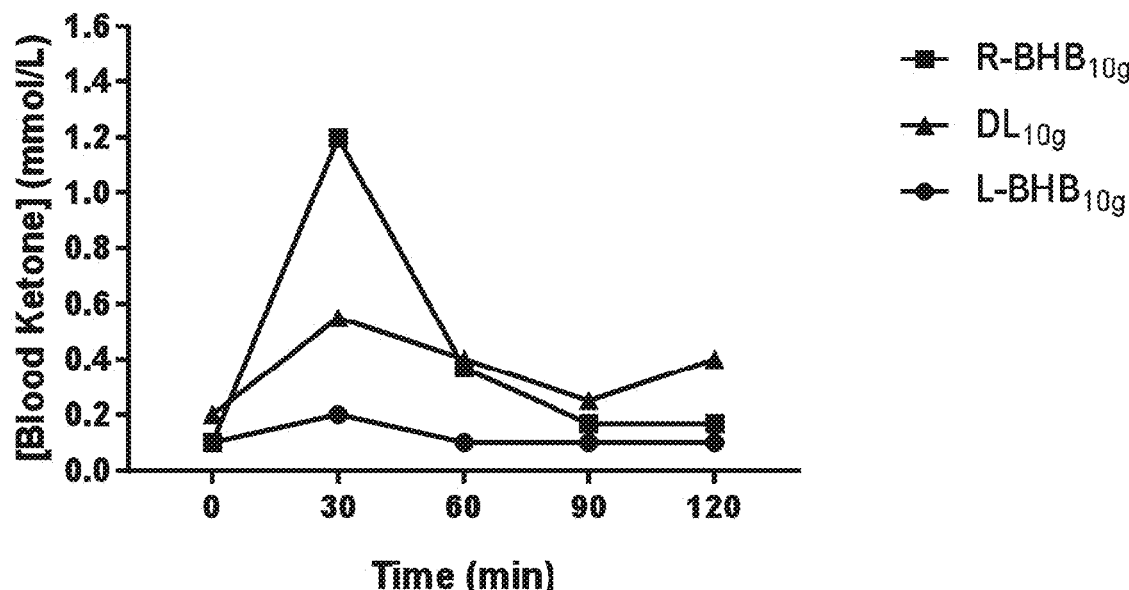
FIG. 10 illustrates a chart illustrating blood ketone levels following an implementation of an example administration protocol.
Figure 11:
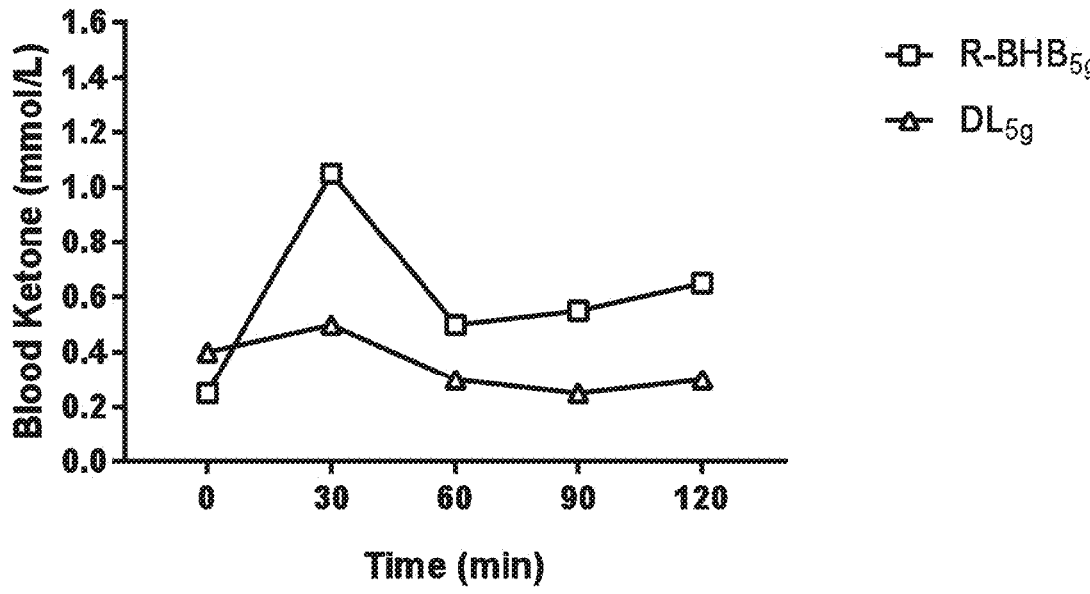
FIG. 11 illustrates a chart illustrating blood ketone levels following an implementation of an example administration protocol.

Individuals were 5 g or 10 mg of R-beta-hydroxybutyrate, L-beta-hydroxybutyrate, or D,L-beta-hydroxybutyrate and blood ketone levels were measured. FIGS. 10 and 11 illustrate the measured blood ketone levels. As illustrated, administration of R-beta-hydroxybutyrate may decrease ketone levels (see e.g., FIGS. 11A and 11B). The reduction of ketone levels occurs even when R-beta-hydroxybutyrate is administered at a dosage of less than 10 g (e.g., approximately 5 g). In addition, unexpectedly (e.g., since it was expected that both the D and L forms of R-beta-hydroxybutyrate behaved in a similar manner), administration of L-beta-hydroxybutyrate does not decrease blood ketones. Furthermore, unexpectedly, even D,L-beta-hydroxybutyrate does not lower blood ketone levels to the same extent as R-beta-hydroxybutyrate. This indicates that L-beta-hydroxybutyrate may block some of the impact of R-beta-hydroxybutyrate, which is unexpected.

Example 11

Figure 12A:
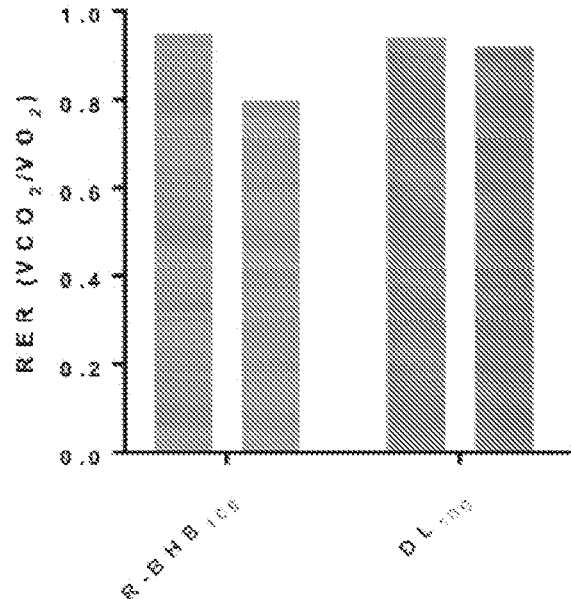
FIG. 12A illustrates a chart illustrating RER levels following an implementation of an example administration protocol.
Figure 12B:
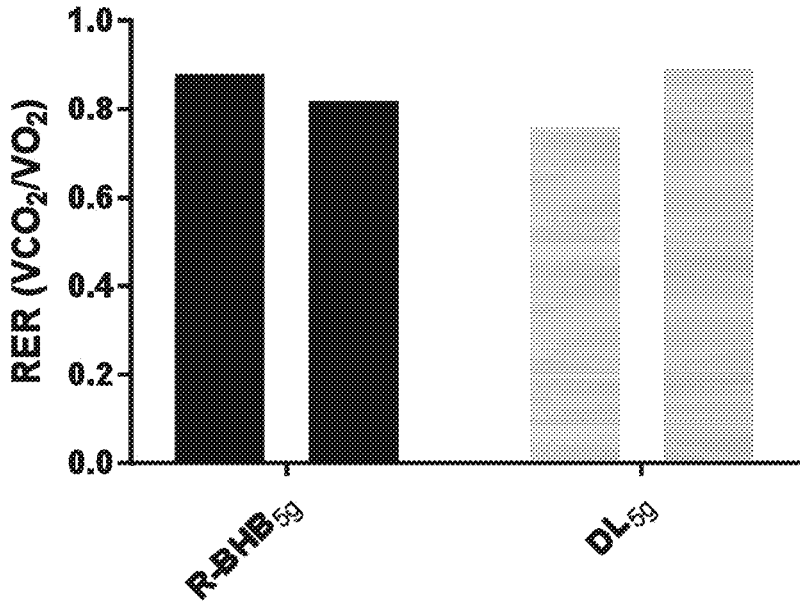
FIG. 12B illustrates a chart illustrating RER levels following an implementation of an example administration protocol.

10 subjects were administered approximately 5 g or 10 g of D,L-beta-hydroxybutyrate or R-beta-hydroxybutyrate, and respiratory exchange ratio was examined (RER, a ratio of carbon dioxide/oxygen). Generally, a ratio of 1.0 indicates that 100% carbohydrate is used as fuel and at 0.7, 100% fat is used as fuel. As illustrated in FIG. 12A, at 10 g, R-beta-hydroxybutyrate administration reduces RER approximately 3× more than D,L-beta-hydroxybutyrate. As illustrated in FIG. 12B, 5 g of R-beta-hydroxybutyrate is capable of achieving a result that even more D,L-beta-hydroxybutyrate is unable to (e.g., D,L-beta-hydroxybutyrate increases RER by 17% rather than decreasing RER).

Example 12

Figure 13C:
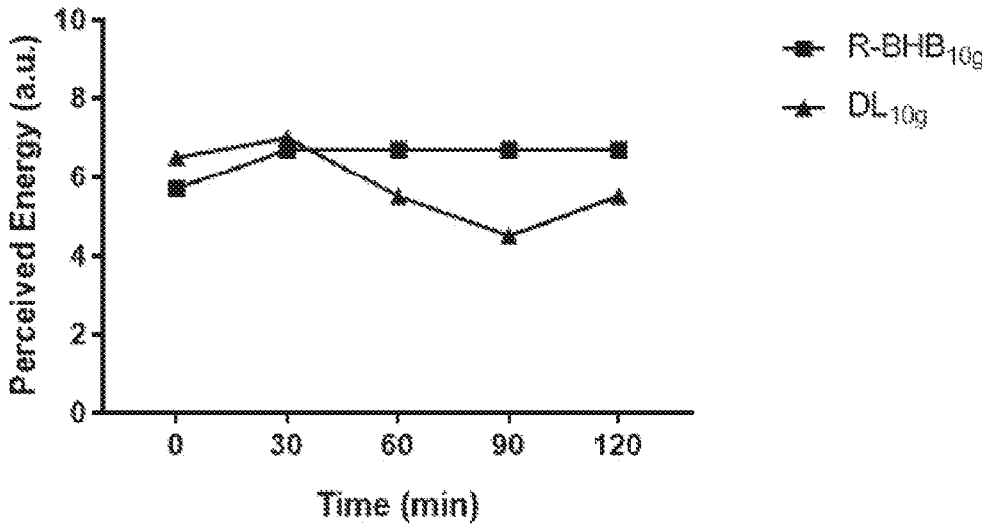
FIG. 13C illustrates a chart illustrating perceived energy following an implementation of an example administration protocol.

Individuals were administered 5 g-10 g of D,L-beta-hydroxybutyrate or R-beta-hydroxybutyrate and tested for perceived hunger, satiety, and perceived energy. FIGS. 13A-13C illustrate the results of the testing. FIG. 13A illustrates perceived hunger, FIG. 13B illustrates perceived satiety, and FIG. 13C illustrates perceived energy. As illustrated in FIG. 13B, at 30 minutes post consumption R-beta-hydroxybutyrate improved satiety levels 2.3 times better than DL-beta-hydroxybutyrate relative to baseline levels. As illustrated in FIG. 13C, R-beta-hydroxybutyrate improved perceived energy from O to 30 minutes post consumption by double that of D,L-beta-hydroxybutyrate. R-beta-hydroxybutyrate sustained elevated perceived energy levels from O minutes at 60, 90, and 120 minutes post consumption, as opposed to D,L-beta-hydroxybutyrate. As illustrated, R-beta-hydroxybutyrate was able to raise perceived energy by 18% and sustain it for 2 hours post ingestion (e.g., more than 2 times greater than the peak value of increase with the DL-beta-hydroxybutyrate)

Example 13

Five (5) young (20s) resistance trained males lifting 50% of their 1-RM on Bench Presses were tested before and after administration of 5 g of R-beta-hydroxybutyrate or D,L- beta-hydroxybutyrate. FIGS. 14A-B illustrate the results of the testing. As illustrated, R-beta-hydroxybutyrate administration resulted in an 11% increase, while DL-beta-hydroxybutyrate administration resulted in only a 2% decrease. Thus, R-beta-hydroxybutyrate experienced a greater than expected impact when compared with D,L-beta-hydroxybutyrate.

The individuals were also tested for power. FIG. 14C illustrates the results of the testing (e.g., averages of power measurements). As illustrated, R-beta-hydroxybutyrate administration increased minimum power by 26%, while the DL-beta-hydroxybutyrate administration raised power by 2%.

Example 14

Individuals were tested for mental acuity before and after administration of 5-10 g of R-beta-hydroxybutyrate or D,L-beta-hydroxybutyrate. Circular Tracking testing (e.g., to assess their cognitive function) was performed and administration of DL-beta-hydroxybutyrate (e.g., 10 g) caused no improvement while the R-beta-hydroxybutyrate (e.g., 10 g) administration caused approximately 3% improvement in tracking accuracy. Vertical Tracking testing (e.g., to assess their cognitive function) was performed and administration of D,L-beta-hydroxybutyrate (e.g., 10 g) improved performance by 4.6%, while the administration of R-beta-hydroxybutyrate (e.g., 10 g) improved performance by 13.8%, which is approximately 3 times greater improvement. Horizontal Saccades testing was performed (e.g., a saccade is one eye movement and known to become significantly slower if cognitive function declines and improve if cognitive function improves). In the horizontal saccades testing, performance improvements were 4 times greater with the administration of R-beta-hydroxybutyrate (e.g., 5 g) than with administration of D,L-beta-hydroxybutyrate (e.g., 13.8% vs. 3.2%). Processing speed testing was performed (e.g., processing speed is considered a true measure of cognitive performance). Administration of R-beta-hydroxybutyrate (e.g., 5 g) improved processing speed by 27.7% and only approximately 18% with administration of the DL-beta-hydroxybutyrate (e.g., 5 g). Response accuracy was also tested. Administration of R-beta-hydroxybutyrate (e.g., 5 g) increased accuracy by 37 percentage points when compared to 12.7% when D,L-beta-hydroxybutyrate was administered.

Thus, administration of R-beta-hydroxybutyrate increased mental acuity more than a similar amount of D,L-beta-hydroxybutyrate. In fact, as the testing revealed, the administration of R-beta-hydroxybutyrate increased mental acuity often by than double when compared with a similar amount of D,L-beta-hydroxybutyrate.

Example 15A

Figure 15:
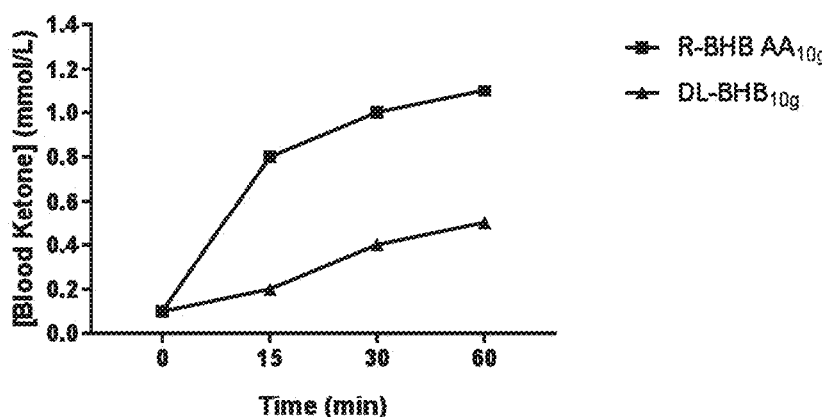
FIG. 15 illustrates a chart illustrating blood ketone levels following an implementation of an example administration protocol.

The compound for administration was prepared to include an R-beta-hydroxybutyrate amino acid complex. An R-beta-hydroxybutyrate-agmatine complex was prepared and an R-beta-hydroxybutyrate-arginine complex was prepared. FIG. 15 illustrates the average blood ketone levels achieved with the R-beta-hydroxybutyrate amino acid complex (e.g., an average of both complexes) when compared with D,L-beta-hydroxybutyrate. As illustrated, blood ketone levels are not only more than double the blood ketone levels achieved with the same quantity of D,L-beta-hydroxybutyrate as R-beta-hydroxybutyrate amino acid complex (e.g., 10 g), but they are more than an additive result of a similar amount of R-beta-hydroxybutyrate and amino acid.

Use of the R-beta-hydroxybutyrate amino acid complex may reduce the amount of cation delivered (e.g. since the complex may deliver the R-beta-hydroxybutyrate rather than a R-beta-hydroxybutyrate salt). The reduction of this cation may decrease side effects (e.g., from increased sodium, potassium, and/or magnesium intake), increase user satisfaction, and/or increase the population that can tolerate the administration of R-beta-hydroxybutyrate (e.g., since some individuals may not be capable of increasing loads of these cations due to underlying diseases and/or disorder). The use of the R-beta-hydroxybutyrate amino acid complex may also allow a higher yield of R-beta-hydroxybutyrate to be administered (90.8% R-beta-hydroxybutyrate, 5% amino acid) when compared with a similar weight of R-beta-hydroxybutyrate salt (e.g., average of 83% yield for BHB sodium).

Example 15B

The compound for administration in Example 15A is modified to be an R-beta-hydroxybutyrate covalently bonded (i.e., coupled) to the amino acid, such as by an ester formed between the hydroxyl group of beta-hydroxybutyrate and carboxyl group of the amino acid and/or an amide formed between the carboxyl group of beta-hydroxybutyrate and amine group of the amino acid. An R-beta-hydroxybutyrate-agmatine compound was prepared and an R-beta-hydroxybutyrate-arginine compound was prepared. FIG. 15 illustrates the expected average blood ketone levels achieved with the R-beta-hydroxybutyrate amino acid compound (e.g., an average of both compounds) when compared with D,L-beta-hydroxybutyrate. As illustrated, blood ketone levels are not only more than double the blood ketone levels achieved with the same quantity of D,L-beta-hydroxybutyrate as R-beta-hydroxybutyrate amino acid compound (e.g., 10 g), but they are more than an additive result of a similar amount of R-beta-hydroxybutyrate and amino acid.

Use of the R-beta-hydroxybutyrate-amino acid compound may reduce the amount of cation delivered (e.g. since the complex may deliver the R-beta-hydroxybutyrate rather than a R-beta-hydroxybutyrate salt). The reduction of this cation may decrease side effects (e.g., from increased sodium, potassium, and/or magnesium intake), increase user satisfaction, and/or increase the population that can tolerate the administration of R-beta-hydroxybutyrate (e.g., since some individuals may not be capable of increasing loads of these cations due to underlying diseases and/or disorder). The use of the R-beta-hydroxybutyrate amino acid compound may also allow a higher yield of R-beta-hydroxybutyrate to be administered (90.8% R-beta-hydroxybutyrate, 5% amino acid) when compared with a similar weight of R-beta-hydroxybutyrate salt (e.g., average of 83% yield for BHB sodium).

Example 16A

Figure 16:
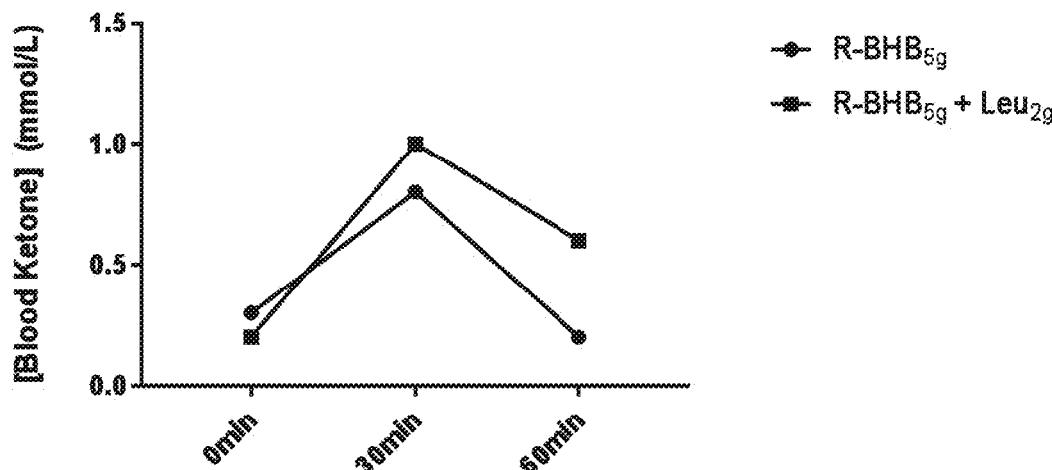
FIG. 16 illustrates a chart illustrating blood ketone levels following an implementation of an example administration protocol.

A composition for administration may include R-beta-hydroxybutyrate and an amino acid, such as leucine. The R-beta-hydroxybutyrate and leucine may be complexed and/or mixed together for administration. The R-beta-hydroxybutyrate and leucine may be administered separately but approximately concurrently. FIG. 16 illustrates the blood ketone levels after administration of R-beta-hydroxybutyrate (5 g) and leucine (2 g). As illustrated, the administration of R-beta-hydroxybutyrate and leucine causes greater elevation of blood ketone levels than the administration of R-beta-hydroxybutyrate (5 g). The administration of R-beta-hydroxybutyrate and leucine causes greater elevation of blood ketone levels than merely the additive effect of similar quantities of R-beta-hydroxybutyrate and leucine administered separately.

Example 16B

The compound for administration in Example 16A is modified to be an R-beta-hydroxybutyrate covalently bonded (i.e., coupled) to the amino acid, such as by an ester linkage formed between the hydroxyl group of beta-hydroxybutyrate and carboxyl group of the amino acid and/or an amide formed between the carboxyl group of beta-hydroxybutyrate and amine group of the amino acid. An R-beta-hydroxybutyrate leucine compound was prepared for administration, with an additional quantity of free R-beta-hydroxybutyrate to form an. R-beta-hydroxybutyrate leucine composition. FIG. 16 illustrates the expected blood ketone levels after administration of R-beta-hydroxybutyrate (5 g) and leucine (2 g). As illustrated, the administration of the R-beta-hydroxybutyrate leucine composition is expected to cause greater elevation of blood ketone levels than the administration of R-beta-hydroxybutyrate (5 g). The administration of the R-beta-hydroxybutyrate leucine composition causes greater elevation of blood ketone levels than merely the additive effect of similar quantities of R-beta-hydroxybutyrate and leucine administered separately.

The following examples provide additional details for how the various beta-hydroxybutyrate-amino acid compounds discloses herein provide specific benefits and synergies.

Increased Energy and Enhanced Ketosis

Example 17

A composition for administration to a subject includes beta-hydroxybutyrate complexed with and/or covalently bonded to isoleucine to form a beta-hydroxybutyrate-isoleucine compound. Apart from having greater bioavailability and being able to travel deeper into the digestive tract compared to other forms of beta-hydroxybutyrate, the isoleucine component boosts endurance by increasing glucose uptake and utilization. The beta-hydroxybutyrate-isoleucine compound also results in the following synergy: isoleucine supports beta-hydroxybutyrate's role in sustained energy delivery during exercise, improving endurance.

Example 18

A composition for administration to a subject includes beta-hydroxybutyrate complexed with and/or covalently bonded to valine to form a beta-hydroxybutyrate-valine compound. Apart from having greater bioavailability and being able to travel deeper into the digestive tract compared to other forms of beta-hydroxybutyrate, the valine component provides energy to muscles and prevents fatigue. The beta-hydroxybutyrate-valine compound also results in the following synergy: valine combines with beta-hydroxybutyrate's ketone energy to reduce exercise fatigue and increase performance.

Example 19

A composition for administration to a subject includes beta-hydroxybutyrate complexed with and/or covalently bonded to glutamine to form a beta-hydroxybutyrate-glutamine compound. Apart from having greater bioavailability and being able to travel deeper into the digestive tract compared to other forms of beta-hydroxybutyrate, the glutamine component enhances gut and immune function during stress. The beta-hydroxybutyrate-glutamine compound also results in the following synergy: glutamine pairs with beta-hydroxybutyrate's anti-inflammatory effects to support immunity and recovery during extended fasting or ketosis. Enhanced Cognitive and Neurological Function

Example 20

A composition for administration to a subject includes beta-hydroxybutyrate complexed with and/or covalently bonded to tryptophan to form a beta-hydroxybutyrate-tryptophan compound. Apart from having greater bioavailability and being able to travel deeper into the digestive tract compared to other forms of beta-hydroxybutyrate, the tryptophan component is a precursor to serotonin and melatonin, supporting mood and sleep. The beta-hydroxybutyrate-tryptophan compound also results in the following synergy: tryptophan combines with beta-hydroxybutyrate's ability to cross the blood-brain barrier and enhance cognitive function to improve mood and sleep regulation.

Example 21

A composition for administration to a subject includes beta-hydroxybutyrate complexed with and/or covalently bonded to tyrosine to form a beta-hydroxybutyrate-tyrosine compound. Apart from having greater bioavailability and being able to travel deeper into the digestive tract compared to other forms of beta-hydroxybutyrate, the tyrosine component is a precursor to dopamine, norepinephrine, and epinephrine, enhancing focus and alertness. The beta-hydroxybutyrate-tyrosine compound also results in the following synergy: tyrosine amplifies beta-hydroxybutyrate's role in improving mental clarity and energy through dopaminergic pathways.

Example 22

A composition for administration to a subject includes beta-hydroxybutyrate complexed with and/or covalently bonded to phenylalanine to form a beta-hydroxybutyrate-phenylalanine compound. Apart from having greater bioavailability and being able to travel deeper into the digestive tract compared to other forms of beta-hydroxybutyrate, the phenylalanine component supports neurotransmitter production and mood regulation. The beta-hydroxybutyrate-phenylalanine compound also results in the following synergy: phenylalanine pairs with beta-hydroxybutyrate's neurological benefits to treat cognitive disorders or stress-induced mental fatigue.

Example 23

A composition for administration to a subject includes beta-hydroxybutyrate complexed with and/or covalently bonded to glycine to form a beta-hydroxybutyrate-glycine compound. Apart from having greater bioavailability and being able to travel deeper into the digestive tract compared to other forms of beta-hydroxybutyrate, the glycine component acts as a calming neurotransmitter and supports connective tissue repair. The beta-hydroxybutyrate-glycine compound also results in the following synergy: glycine amplifies beta-hydroxybutyrate's anti-inflammatory and neuroprotective properties for stress reduction and tissue healing.

Increased Muscle and Physical Performance

Example 24

A composition for administration to a subject includes beta-hydroxybutyrate complexed with and/or covalently bonded to leucine to form a beta-hydroxybutyrate-leucine compound. Apart from having greater bioavailability and being able to travel deeper into the digestive tract compared to other forms of beta-hydroxybutyrate, the leucine component promotes muscle protein synthesis and recovery. The beta-hydroxybutyrate-leucine compound also results in the following synergy: combines beta-hydroxybutyrate's role in energy metabolism with leucine's anabolic effects to enhance recovery and muscle building in ketosis.

Example 25

A composition for administration to a subject includes beta-hydroxybutyrate complexed with and/or covalently bonded to arginine to form a beta-hydroxybutyrate-arginine compound. Apart from having greater bioavailability and being able to travel deeper into the digestive tract compared to other forms of beta-hydroxybutyrate, the arginine component improves nitric oxide production, enhancing blood flow and nutrient delivery. The beta-hydroxybutyrate-arginine compound also results in the following synergy: arginine works with beta-hydroxybutyrate to optimize muscle performance and recovery by enhancing oxygen and nutrient delivery during ketosis.

Example 26

A composition for administration to a subject includes beta-hydroxybutyrate complexed with and/or covalently bonded to citrulline to form a beta-hydroxybutyrate-citrulline compound. Apart from having greater bioavailability and being able to travel deeper into the digestive tract compared to other forms of beta-hydroxybutyrate, the citrulline component converts to arginine, extending nitric oxide effects. The beta-hydroxybutyrate-citrulline compound also results in the following synergy: supports sustained energy and recovery during high-performance activities.

Example 27

A composition for administration to a subject includes beta-hydroxybutyrate complexed with and/or covalently bonded to beta-alanine to form a beta-hydroxybutyrate-beta-alanine compound. Apart from having greater bioavailability and being able to travel deeper into the digestive tract compared to other forms of beta-hydroxybutyrate, the beta-alanine component increases muscle carnosine levels, reducing fatigue. The beta-hydroxybutyrate-beta-alanine compound also results in the following synergy: beta-alanine pairs with beta-hydroxybutyrate's ATP-sparing effects to delay muscle fatigue during high-intensity exercise.

Enhanced Metabolic and Cellular Repair

Example 28

A composition for administration to a subject includes beta-hydroxybutyrate complexed with and/or covalently bonded to lysine to form a beta-hydroxybutyrate-lysine compound. Apart from having greater bioavailability and being able to travel deeper into the digestive tract compared to other forms of beta-hydroxybutyrate, the lysine component is essential for collagen synthesis and cellular repair. The beta-hydroxybutyrate-lysine compound also results in the following synergy: lysine amplifies beta-hydroxybutyrate's role in reducing oxidative stress to promote faster tissue repair and recovery.

Example 29

A composition for administration to a subject includes beta-hydroxybutyrate complexed with and/or covalently bonded to proline to form a beta-hydroxybutyrate-proline compound. Apart from having greater bioavailability and being able to travel deeper into the digestive tract compared to other forms of beta-hydroxybutyrate, the proline component is key for collagen production and skin health. The beta-hydroxybutyrate-proline compound also results in the following synergy: enhances anti-aging properties by repairing connective tissue.

Example 30

A composition for administration to a subject includes beta-hydroxybutyrate complexed with and/or covalently bonded to methionine to form a beta-hydroxybutyrate-methionine compound. Apart from having greater bioavailability and being able to travel deeper into the digestive tract compared to other forms of beta-hydroxybutyrate, the methionine component is an antioxidant that aids in detoxification and reduces oxidative stress. The beta-hydroxybutyrate-methionine compound also results in the following synergy: methionine amplifies beta-hydroxybutyrate's ability to combat oxidative stress, protecting cells from damage.

Example 31

A composition for administration to a subject includes beta-hydroxybutyrate complexed with and/or covalently bonded to threonine to form a beta-hydroxybutyrate-threonine compound. Apart from having greater bioavailability and being able to travel deeper into the digestive tract compared to other forms of beta-hydroxybutyrate, the threonine component supports protein balance and immune function. The beta-hydroxybutyrate-threonine compound also results in the following synergy: threonine pairs with beta-hydroxybutyrate's anti-inflammatory effects for better immune resilience.

Improved Detoxification and Gut Health

Example 32

A composition for administration to a subject includes beta-hydroxybutyrate complexed with and/or covalently bonded to taurine to form a beta-hydroxybutyrate-taurine compound. Apart from having greater bioavailability and being able to travel deeper into the digestive tract compared to other forms of beta-hydroxybutyrate, the taurine component supports bile acid production and liver detoxification. The beta-hydroxybutyrate-taurine compound also results in the following synergy: enhances the liver's efficiency in utilizing ketones for energy and detoxifying harmful substances.

Example 33

A composition for administration to a subject includes beta-hydroxybutyrate complexed with and/or covalently bonded to ornithine to form a beta-hydroxybutyrate-ornithine compound. Apart from having greater bioavailability and being able to travel deeper into the digestive tract compared to other forms of beta-hydroxybutyrate, the ornithine component facilitates urea cycle and detoxification. The beta-hydroxybutyrate-ornithine compound also results in the following synergy: ornithine combines with beta-hydroxybutyrate to reduce ammonia accumulation during protein metabolism, improving endurance.

Example 33

Any of the foregoing examples is modified to include acetoacetate in addition to or in place of at least some of the beta-hydroxybutyrate. Because acetoacetate is a ketone body that can be metabolized similar to, and/or converted into, beta-hydroxybutyrate, similar results would be reasonably expected. The acetoacetate can be complexed with and/or covalently bonded to the amino acid.

Example 34

Any of the foregoing examples is modified to include 1,3-butanediol in addition to or in place of at least some of the beta-hydroxybutyrate or acetoacetate. Because 1,3-butanediol can be readily metabolized and converted into beta-hydroxybutyrate similar results would be reasonably expected. The 1,3-butanediol can be complexed with and/or covalently bonded to the amino acid.

Example 35

Any of the foregoing examples is modified to include one or more medium chain fatty acids in addition to or in place of at least some of the beta-hydroxybutyrate, acetoacetate, or 1,3-butanediol. Because medium chain fatty acids can be readily metabolized and converted into beta-hydroxybutyrate and/or acetoacetate, similar results would be reasonably expected. The one or more medium chain fatty acids can be complexed with and/or covalently bonded to the amino acid.

End of Examples

In some implementations, one or more additives may be included in the composition, such as flavorings (e.g., natural and/or artificial), vitamins, minerals, binders, and/or any other appropriate additive. The additives may alter flavor, color, and/or texture. The additives may increase palatability and/or facilitate inclusion in a delivery vehicle (e.g., tablet, food product, beverage product such as a drink mix, etc.). The additive may be any appropriate solid and/or liquid to which the compound is added. For example, an additive may include liquid carriers, such as water, milk(s), and/or any other appropriate drinkable liquid. In some implementations, the composition may include a pharmaceutically inert liquid carrier, such as water (e.g., tap water, filtered water, distilled water, etc.). The liquid carrier may include other drinkable liquids such as coconut water, watermelon water, electrolyte water, and/or combinations thereof. The liquid carrier may include milks such as dairy milk, non-dairy milk, coconut milk, other milks, and/or combinations thereof. The liquid carrier may include an electrolyte solution, in some implementations.

The described compositions may be administered via any appropriate administration method. For example, the described compositions may be administered enterally and/or parenterally. In some implementations, the described composition may be administered via a tablet and/or capsule. The described composition may be provided in a powdered form that allows the described composition to be sprinkled on food, mixed with a liquid to provide a beverage, and/or directly administered. The described composition may be provided in gel form. The compounds in the composition may be mixed, coupled to each other, and/or provided separately. For example, the composition may include beta-hydroxybutyrate coupled to another compound (e.g., beta-hydroxybutyrate ester and/or amino acid). In some implementations, the beta-hydroxybutyrate and one or more other compounds may be provided separately (e.g., in pills). An individual may sequentially and/or concurrently be administered (e.g., swallow pills) the beta-hydroxybutyrate and other compounds.

The described compositions may be administered on an administration protocol to cause weight loss and/or maintain a weight of an individual; elevate and/or maintain blood ketone levels; increase and/or maintain ketosis; and/or improve glucose tolerance (e.g., fasting glucose levels may be reduced and/or glucose metabolism may be improved), in some implementations. For example, the described compositions may be administered once a day, via an extended-release preparation, and/or multiple times a day (e.g., 1 to 5 times a day, 2 to 5 times a day, 3 to 5 times a day, etc.). The described composition may replace other pharmaceuticals or dietary supplements taken to promote weight loss, maintain a weight, promote ketosis, elevate blood ketone levels and/or be utilized in combination with one or more other pharmaceuticals or dietary supplements, as appropriate. The described composition may replace other pharmaceuticals or dietary supplements taken for improving glucose tolerance, such as metformin, and/or be utilized in combination with one or more other pharmaceuticals or dietary supplements, as appropriate, in some implementations.

In various implementations, the described composition(s) (e.g., butyrate, beta-hydroxybutyrate, R-beta-hydroxybutyrate, related compounds, and/or one or more other compounds) may include one or more of the described components, equivalent(s) of the described component(s), derivatives of the described component(s), complex(es) of the described component(s), salt(s) of the described component(s), and/or combinations thereof.

In various implementations, a pharmaceutically effective amount of one or more of the described composition(s) may be administered. Administration of the pharmaceutically effective amount may induce and/or maintaining ketosis; maintaining and/or promoting weight loss; increase mental processes (e.g., acuity including cognitive functioning, mood, energy, alertness, focus, performance, effects of aging, etc.); improve and/or maintain body composition; function as a therapeutic for one or more of the described conditions or disorders (e.g., treat neurological disorders); and/or combinations thereof.

Although various types of increases in mental acuity have been described, other features of mental acuity such as memory, focus, concentration, and/or understanding (e.g., speed of processing, accuracy of processing) may be increased by administration of an effective amount of the composition that includes R-beta-hydroxybutyrate.

Although a subject and/or an individual have been described as a human, a subject and/or individual may be a person or a group of people. Although various described systems and processes have been described as a being administered in humans, the described systems and processes may be administered to other mammals, such as rats, dogs, etc.

In various implementations, beta-hydroxybutyrate may administered simultaneously and/or sequentially with one or more other compounds (e.g., short chain, medium chain, and/or long chain fatty acids). For example, beta-hydroxybutyrate and/or one or more other compounds may be delivered mixed in a powdered, liquid, gel, and/or other appropriate form. In some implementations, the beta-hydroxybutyrate and/or one or more other compounds may be administered via pills, tablets, capsules, other oral administration forms, intravenously, nasal sprays, sublingual tabs/strips, or topical delivery, rectal, other appropriate administration forms, and/or combinations thereof.

Although the term beta-hydroxybutyrate is the terminology used in the described implementations, beta-hydroxybutyrate is also referred to as beta-hydroxybutyrate, (R)-3-Hydroxybutyric acid, (R)-3-Hydroxybutanoic acid, (3R)-3-hydroxybutanoic acid, (R)-3-Hydroxybutanoate, (R)-(–)-3-Hydroxybutyric acid, (R)-(–)-beta-hydroxybutyric acid, 3-D-hydroxybutyrate, BHIB, BHB, 3-delta-hydroxybutyrate, delta-3-hydroxybutyrate, 3-D-hydroxybutyric acid, D-3-hydroxybutyric acid, 3R-hydroxybutanoic acid, delta-beta-hydroxybutyrate, D-3-hydroxybutyrate, D-(–)-3-hydroxybutyrate, delta-3-hydroxybutyric acid, (–)-3-Hydroxybutyric acid, D-beta-hydroxybutyrate, (R)-(–)-b-Hydroxybutyrate, (R)-beta-Hydroxybutyric acid, delta-(–)-3-hydroxybutyrate, (R)-3-hydroxybutyrate, (R)-beta-hydroxybutanoic acid, (R)-(–)-beta-hydroxybutyrate, (–)-3-Hydroxy-n-butyric acid, (R)-(–)-β-hydroxybutyric acid, butanoic acid, 3-hydroxy-, (R)-butyric acid, 3-hydroxy-, D-(–)-(R)-3-82578-46-9, beta-D-hydroxybutyric acid, D-beta-hydroxybutyric acid, (3R)-3-delta-hydroxybutyric acid, 3-(R)-hydroxybutyric acid, and/or (–)-beta-hydroxybutyrate.

In various implementations, beta-hydroxybutyrate is described as included in a composition; administered in an amount, form, and/or schedule; and/or being in a particular form (e.g., complexed and/or coupled). R-beta-hydroxybutyrate may be utilized in the various described implementations of beta-hydroxy butyrate in the same or lower amount as the described beta-hydroxybutyrate, as appropriate.

It is to be understood the implementations are not limited to particular systems or processes described which may, of course, vary. It is also to be understood that the terminology used herein is for the purpose of describing particular implementations only and is not intended to be limiting. As used in this specification, the singular forms "a", "an" and "the" include plural referents unless the content clearly indicates otherwise. Thus, for example, reference to "a compound" includes a combination of two or more compounds and reference to "a beta-hydroxybutyrate" includes different types and/or combinations of beta-hydroxybutyrate.

Although the present disclosure has been described in detail, it should be understood that various changes, substitutions and alterations may be made herein without departing from the spirit and scope of the disclosure as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure, processes, machines, manufacture, compositions of matter, means, methods, or steps, presently existing or later to be developed that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

The invention claimed is:

1. A composition for administering ketone bodies to a subject, comprising:
   a ketone body component including a ketone body, ketone body precursor, or combination thereof; and
   an amino acid component including at least one amino acid,
   wherein at least a portion of the ketone body component is complexed with and/or coupled to at least a portion of the at least one amino acid component.

2. The composition of claim 1, wherein the composition comprises a complex of the ketone body component and the amino acid component.

3. The composition of claim 1, wherein the composition comprises a compound of, including a covalent bond between, the ketone body component and the amino acid component.

4. The composition of claim 1, wherein the amino acid component includes at least one amino acid selected from the group consisting of leucine, lysine, arginine, histidine, ornithine, creatine, agmatine, citrulline, isoleucine, valine, glutamine, tryptophan, tyrosine, phenylalanine, glycine, beta-alanine, proline, methionine, threonine, and taurine.

5. The composition of claim 1, wherein the ketone body component includes at least one of beta-hydroxybutyrate or acetoacetate in acid, salt and/or ester form.

6. The composition of claim 1, wherein the ketone body component includes R-beta-hydroxybutyrate and S-beta-hydroxybutyrate, and wherein the composition is enriched with the R-beta-hydroxybutyrate relative to the S-beta-hydroxybutyrate.

7. The composition of claim 1, wherein the ketone body component includes greater than approximately 90% R-beta-hydroxybutyrate and less than approximately 10% S-beta-hydroxybutyrate, or greater than approximately 95% R-beta-hydroxybutyrate and less than approximately 5% S-beta-hydroxybutyrate, or greater than approximately 99% R-beta-hydroxybutyrate and less than approximately 1% S-beta-hydroxybutyrate.

8. The composition of claim 1, wherein the ketone body precursor includes 1,3-butanediol or ester thereof.

9. The composition of claim 1, wherein the ketone body precursor includes at least one medium chain fatty acid or ester thereof.

10. The composition of claim 1, wherein the composition provides a dose of from approximately 0.1 g to approximately 50 g of the ketone body component.

11. The composition of claim 1, wherein the composition provides a dose of from about 0.1 g to about 20 g of the ketone body component.

12. The composition of claim 1, wherein the composition provides a dose of from about 10 g to about 30 g of the ketone body component.

13. The composition of claim 1, wherein the composition provides a dose of from approximately 0.5 g to approximately 10 g of the amino acid component.

14. The composition of claim 1, wherein the composition provides a dose of from approximately 0.5 g to approximately 2 g of the amino acid component.

15. The composition of claim 1, further comprising at least one additive selected from the group consisting of butyrate, butyric acid, tributyrin, short-chain fatty acids, esters of short-chain fatty acids, berberine, berberine metabolites, amino acid metabolites, vitamins, minerals, coconut milk powder, flavorings, caffeine, theacrine, colorings, binders, electrolytes, tetrahydrobiopterin, nucleic acids, alpha-ketoglutaric acid, alpha lipoic acid, nutritional co-factors, beta-methyl-beta-hydroxybutyrate, arginine alpha-ketoglutarate, R-alpha lipoic acid, thiamine, NAD+, NADH, riboflavin, FAD+, FADH, riboflavin-5-phosphate, niacin, nicotinic acid, niacinamide, inositol hexanicotinate, pyridoxine, pyridoxal, pyridoxamine, ascorbic acid, ascorbate salts, citric acid, malic acid, sodium benzoate, pyridoxal-5-phosphate, methylcobalamin, cyanocobalamin, adenosylcobalamin, hydroxycobalamin, pantothenic acid, pantetheine, potassium sorbate, acesulfame K, aspartame, sucralose, stevia, monk fruit extract, allulose, prebiotic fibers, xylo-oligosaccharides (XOS), galacto-oligosaccharides (GOS), mannan-oligosaccharides (MOS), isomalto-oligosaccharides (IMO), lipo-oligosaccharides (LOS), xanthan gum, organic gums, thickeners, and suspension agents.

16. The composition of claim 1, wherein the ketone body is selected from the group consisting of beta-hydroxybutyric acid, acetoacetic acid, beta-hydroxybutyrate salts, acetoacetate salts, beta-hydroxybutyrate esters, acetoacetate esters, and combinations thereof.

17. A method of administering ketone bodies to a subject in need thereof comprising administering the composition of claim 1 to the subject, wherein the composition causes or results in at least one of weight loss, weight maintenance, reduced blood glucose level, maintenance of blood glucose level, increased muscle and physical performance, enhanced metabolic and cellular repair, improved detoxification and gut health, targeted bioavailability, sustained release and controlled absorption, increased metabolic efficiency, enhanced cellular uptake, minimized side effects, multifunctional therapeutics, improved focus, improved energy, improved cognitive function, improved mental acuity, treatment of traumatic brain injury, treatment of diabetes, treatment of neurological disorder, treatment of cancer, treatment of inflammatory condition, appetite suppression, anti-aging effects, anti-glycation effects, treatment of epilepsy, treatment of depression, improved performance, improved muscle mass, improved motor function, increased strength, increased metabolism, increased fat loss, increased fat oxidation, improved body composition, and improved mood.

18. The method of claim 17, wherein the composition is administered to the subject orally, enterally, parenterally, intravenously, nasally, sublingually, topically, or rectally.

19. A composition for administering ketone bodies and increasing blood ketone level in a subject, comprising:

a ketone body component including a ketone body, ketone body precursor, or combination thereof, and an amino acid component including at least one amino acid selected from the group consisting of leucine, lysine, arginine, histidine, ornithine, creatine, agmatine, citrulline, isoleucine, valine, glutamine, tryptophan, tyrosine, phenylalanine, glycine, beta-alanine, proline, methionine, threonine, and taurine;

wherein at least a portion of the ketone body component is complexed with and/or coupled to at least a portion of the at least one amino acid component.

20. The composition of claim 19, wherein the ketone body includes at least one of beta-hydroxybutyrate or acetoacetate in acid, salt and/or ester form.

21. The composition of claim 19, wherein the ketone body precursor includes at least one of 1,3-butanediol, medium chain fatty acid, or ester thereof.

22. A composition for administering ketone bodies to a subject in need thereof, comprising:

a ketone body component including a ketone body, ketone body precursor, or combination thereof;

an amino acid component including at least one amino acid selected from the group consisting of leucine, lysine, arginine, histidine, ornithine, creatine, agmatine, citrulline, isoleucine, valine, glutamine, tryptophan, tyrosine, phenylalanine, glycine, beta-alanine, proline, methionine, threonine, and taurine, wherein at least a portion of the ketone body component is complexed with and/or coupled to at least a portion of the at least one amino acid component; and at least one additive selected from the group consisting of butyrate, butyric acid, tributyrin, short-chain fatty acids, esters of short-chain fatty acids, berberine, berberine metabolites, amino acid metabolites, vitamins, minerals, coconut milk powder, flavorings, caffeine, theacrine, colorings, binders, electrolytes, tetrahydrobiopterin, nucleic acids, alpha-ketoglutaric acid, alpha lipoic acid, nutritional co-factors, beta-methyl-beta-hydroxybutyrate, arginine alpha-ketoglutarate, R-alpha lipoic acid, thiamine, NAD+, NADH, riboflavin, FAD+, FADH, riboflavin-5-phosphate, niacin, nicotinic acid, niacinamide, inositol hexanicotinate, pyridoxine, pyridoxal, pyridoxamine, ascorbic acid, ascorbate salts, citric acid, malic acid, sodium benzoate, pyridoxal-5-phosphate, methylcobalamin, cyanocobalamin, adenosylcobalamin, hydroxycobalamin, pantothenic acid, pantetheine, potassium sorbate, acesulfame K, aspartame, sucralose, stevia, monk fruit extract, allulose, prebiotic fibers, xylo-oligosaccharides (XOS), galacto-oligosaccharides (GOS), mannan-oligosaccharides (MOS), isomalto-oligosaccharides (IMO), lipo-oligosaccharides (LOS), xanthan gum, organic gums, thickeners, and suspension agents.

\* \* \* \* \*